(12) United States Patent
Tan et al.

(10) Patent No.: US 11,015,190 B2
(45) Date of Patent: May 25, 2021

(54) METHOD OF TREATING A PATIENT HAVING RENAL CANCER

(71) Applicant: Lucence Life Sciences Pte Ltd, Singapore (SG)

(72) Inventors: Min-Han Tan, Singapore (SG); Yukti Choudhury, Singapore (SG); Puay Hoon Tan, Singapore (SG); Bin Tean Teh, Singapore (SG)

(73) Assignee: Lucence Life Sciences Pte Ltd, Singapore (SG)

( * ) Notice: Subject to any disclaimer, the term of this patent is extended or adjusted under 35 U.S.C. 154(b) by 733 days.

(21) Appl. No.: 15/022,917

(22) PCT Filed: Sep. 17, 2014

(86) PCT No.: PCT/SG2014/000446
§ 371 (c)(1),
(2) Date: Mar. 17, 2016

(87) PCT Pub. No.: WO2015/050500
PCT Pub. Date: Apr. 9, 2015

(65) Prior Publication Data
US 2016/0230234 A1 Aug. 11, 2016

(30) Foreign Application Priority Data
Sep. 17, 2013 (SG) ................................ 2013070149

(51) Int. Cl.
*C12Q 1/6886* (2018.01)
*C12N 15/10* (2006.01)

(52) U.S. Cl.
CPC ....... *C12N 15/1072* (2013.01); *C12Q 1/6886* (2013.01); *C12Q 2600/106* (2013.01); *C12Q 2600/118* (2013.01); *C12Q 2600/158* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| 2005/0130193 A1* | 6/2005 | Luxon | G01N 33/6893 435/6.14 |
| 2010/0183593 A1* | 7/2010 | Lenz | C12Q 1/6886 424/133.1 |
| 2011/0171633 A1* | 7/2011 | Cowens | G16B 99/00 435/6.1 |
| 2011/0306514 A1* | 12/2011 | Hewitt | G01N 33/57484 506/9 |

FOREIGN PATENT DOCUMENTS

| WO | WO-2006/066071 A2 | 6/2006 |
| WO | WO-2009/061800 A2 | 5/2009 |
| WO | WO-2011/062634 A2 | 5/2011 |

OTHER PUBLICATIONS

Illunnina Whole Genome HunnanHT-12 v.4.0 Beadchip Kit, May 12, 2010, (Data Analysis Sheet Jan. 11, 2011). (Year: 2011).*
Kozera et al. (J Appl Genet. 2013; 54(4): 391-406). (Year: 2013).*
Glen et al. (BioTechniques, 2007; 43, pp. 639-647) (Year: 2007).*
Kosari (Clin Cancer Res 2005;11(14) Jul. 15, 2005) (Year: 2005).*
Buchner, A. et al., Downregulation of HNF-1B in Renal Cell Carcinoma Is Associated With Tumor Progression and Poor Prognosis, Urology, 76(2): 507.e6-507.e11 (2010).
Hlavkova, D. et al, Monitoring of serum levels of angiogenin, ENA-78 and GRO chemokines in patients with renal cell carcinoma (RCC) in the course of the treatment, Acta Medica, 51(3): 185-190 (2008).
Illumina, Human HT-12 v4 BeadChip Product Information, pp. 1-2 (Jan. 1, 2010).
Jung, M. et al, In search of suitable reference genes for gene expression studies of human renal cell carcinoma by real-time PCR, BMC Molecular Biology, 8(1): 47 (2007).
Kosari, F. et al, Clear cell renal cell carcinoma: gene expression analyses identify a potential signature for tumor aggressiveness, Clinical Cancer Research, 11(14): 5128-5139 (2005).
Lopez-Lago, M.A. et al., Neutrophil chemokines secreted by tumor cells mount a lung antimetastatic response during renal cell carcinoma progression, Oncogene, 32(14): 1752-1760 (2012).
Mestas, J. et al, The Role of CXCR2/CXCR2 Ligand Biological Axis in Renal Cell Carcinoma, The Journal Of Immunology, 175(8): 5351-5357 (2005).
Cho, N.H. et al., Increased expression of matrix metalloproteinase 9 correlates with poor prognostic variables in renal cell carcinoma, European Urology, 44:560-566 (2003).

(Continued)

*Primary Examiner* — Pablo S Whaley
(74) *Attorney, Agent, or Firm* — Choate, Hall & Stewart LLP; Brian E. Reese; Dana M. Daukss

(57) ABSTRACT

A method of making a prognosis as to whether a patient having renal cancer is likely to survive in a tumour tissue sample obtained from the patient is provided. The method comprising determining the level of expression for each marker of a panel of markers comprising at least one housekeeping gene selected from the group consisting of ACTB, RPL13A, RPL9, and RPS29 and any combinations thereof and at least one prognostic gene selected from the group consisting of CXCL5, EFNA5, EMCN, G6PC, GFPT2, HIST2H3C, IGFBP1, LAMB3, MMP9, MOCOS, PLG, PRAME, RARRES1, SDPR, SLC6A19, TK1, KDELR3 and TSPAN7 and any combinations thereof, comparing the level of expression of each marker with a predetermined reference level associated with each marker, and determining the differential expression of each marker in the tumour tissue sample based on the expression parameter for each marker to provide a prognosis for renal cancer.

7 Claims, 8 Drawing Sheets

Specification includes a Sequence Listing.

(56) References Cited

OTHER PUBLICATIONS

Choudhury, Y. et al., A multigene assay identifying distinct prognostic subtypes of clear cell renal cell carcinoma with differential response to tyrosine kinase inhibition, European Urology, 67:17-20 (2015).
Cooper, S.J. et al., Current status of biomarker discovery in human clear cell renal cell carcinoma, Journal of Molecular Biomarkers and Diagnosis, S2:005 (2012).
De Jonge, H.J.M. et al., Evidence based selection of housekeeping genes, PLoS One 2(9):e898 (2007).
Edeline, J. et al., Description of 2 angiogenic phenotypes in clear cell renal cell carcinoma, Human Pathology, 43:1982-1990 (2012).
Glenn, S.T. et al., Expression profiling of archival renal tumors by quantitative PCR to validate prognostic markers, BioTechniques, 43(5):639-647 (2007).
International Search Report for PCT/SG2014/000446, 9 pages (dated Jan. 22, 2015).
Kallakury, B.V.S. et al., Increased expression of matrix metalloproteinases 2 and 9 and tissue inhibitors of metalloproteinases 1 and 2 correlate with poor prognostic variables in renal cell carcinoma, Clinical Cancer Research, 7:3113-3119 (2001).
Lallemant, B. et al., Reference gene selection for head and neck squamous cell carcinoma gene expression studies, BMC Molecular Biology, 10:78 (2009).
Maruschke, M. et al., Identification of potential prognostic markers with gene expression analysis in clear cell renal cell carcinoma (ccRCC), Urology, 78(3A):5234-5235, Abstract UP-01.146 (2011).
Rini, B.I. et al., Identification of prognostic genomic markers in patients with localized clear cell renal cell carcinoma (ccRCC), Journal of Clinical Oncology, 28(15S):4501 (2010).
Schwaab, T. et al., Prediction for and mechanism of response to dendritic cell (DC)-based immunotherapy in metastatic renal cell carcinoma (RCC)-Gene expression profiling of peripheral blood lymphocytes (PBL), Journal of Urology, 183(4):e697, Abstract 1796 (2010).
Thorrez, L. et al., Using ribosomal protein genes as reference: a tale of caution, PLoS One, 3(3):e1854 (2008).
Wang, T.H. et al., EphrinA5 suppresses colon cancer development by negatively regulating epidermal growth factor receptor stability, The FEBS Journal, 279:251-263 (2012).
Written Opinion for PCT/SG2014/000446, 11 pages (dated Jan. 22, 2015).
Yoon, S.Y. et al., Gene expression profiling of human HBV- and/or HCV-associated hepatocellular carcinoma cells using expressed sequence tags, International Journal of Oncology 29:315-327 (2006).
Sawa, Y. and Tsuruga, E., The expression of E-selectin and chemokines in the cultured human lymphatic endothelium with lipopolysaccharides, J. Anat., 212: 654-663 (2008).

\* cited by examiner

C

D

SEQUENCE LISTING

<160> NUMBER OF SEQ ID NOS: 82

<210> SEQ ID NO 1
<211> LENGTH: 19
<212> TYPE: DNA
<213> ORGANISM: Artificial Sequence
<220> FEATURE:
<223> OTHER INFORMATION: AGTR1_v1 Forward Primer

<400> SEQUENCE: 1
gtcggcacca ggtgtattt                                            19

<210> SEQ ID NO 2
<211> LENGTH: 21
<212> TYPE: DNA
<213> ORGANISM: Artificial Sequence
<220> FEATURE:
<223> OTHER INFORMATION: AGTR1_v1 Reverse Primer

<400> SEQUENCE: 2
ccatcttcag tagaagagtt g                                         21

```
<210> SEQ ID NO 3
<211> LENGTH: 21
<212> TYPE: DNA
<213> ORGANISM: Artificial Sequence
<220> FEATURE:
<223> OTHER INFORMATION: AGTR1_v3 Forward Primer

<400> SEQUENCE: 3
gctcagagga ggtgtatttg a                                              21

<210> SEQ ID NO 4
<211> LENGTH: 21
<212> TYPE: DNA
<213> ORGANISM: Artificial Sequence
<220> FEATURE:
<223> OTHER INFORMATION: AGTR1_v3 Reverse Primer

<400> SEQUENCE: 4
ccatcttcag tagaagagtt g                                              21

<210> SEQ ID NO 5
<211> LENGTH: 23
<212> TYPE: DNA
<213> ORGANISM: Artificial Sequence
<220> FEATURE:
<223> OTHER INFORMATION: CTHRC1 Forward Primer

<400> SEQUENCE: 5
gtggtggacc tgtataatgg aat                                            23

<210> SEQ ID NO 6
<211> LENGTH: 18
<212> TYPE: DNA
<213> ORGANISM: Artificial Sequence
<220> FEATURE:
<223> OTHER INFORMATION: CTHRC1 Reverse Primer

<400> SEQUENCE: 6
gaatgccatt ggccccag                                                  18

<210> SEQ ID NO 7
<211> LENGTH: 18
<212> TYPE: DNA
<213> ORGANISM: Artificial Sequence
<220> FEATURE:
<223> OTHER INFORMATION: CXCL5 Forward Primer

<400> SEQUENCE: 7
cgcaaggagt tcatccca                                                  18

<210> SEQ ID NO 8
<211> LENGTH: 17
<212> TYPE: DNA
<213> ORGANISM: Artificial Sequence
<220> FEATURE:
<223> OTHER INFORMATION: CXCL5 Reverse Primer

<400> SEQUENCE: 8
cagggaggct accactt                                                   17

<210> SEQ ID NO 9
<211> LENGTH: 19
<212> TYPE: DNA
<213> ORGANISM: Artificial Sequence
<220> FEATURE:
<223> OTHER INFORMATION: EFNA5 Forward Primer
```

```
<400> SEQUENCE: 9
cagcagatga caccgtaca                                                    19

<210> SEQ ID NO 10
<211> LENGTH: 19
<212> TYPE: DNA
<213> ORGANISM: Artificial Sequence
<220> FEATURE:
<223> OTHER INFORMATION: EFNA5 Reverse Primer

<400> SEQUENCE: 10
caaaaggcgg ctgggtatc                                                    19

<210> SEQ ID NO 11
<211> LENGTH: 24
<212> TYPE: DNA
<213> ORGANISM: Artificial Sequence
<220> FEATURE:
<223> OTHER INFORMATION: EMCN Forward Primer

<400> SEQUENCE: 11
gatcaacctc agtctgataa agag                                              24

<210> SEQ ID NO 12
<211> LENGTH: 20
<212> TYPE: DNA
<213> ORGANISM: Artificial Sequence
<220> FEATURE:
<223> OTHER INFORMATION: EMCN Reverse Primer

<400> SEQUENCE: 12
gtgcagagtg ctcaccagac                                                   20

<210> SEQ ID NO 13
<211> LENGTH: 18
<212> TYPE: DNA
<213> ORGANISM: Artificial Sequence
<220> FEATURE:
<223> OTHER INFORMATION: F2RL3 Forward Primer

<400> SEQUENCE: 13
aggtggtgat gacagcac                                                     18

<210> SEQ ID NO 14
<211> LENGTH: 19
<212> TYPE: DNA
<213> ORGANISM: Artificial Sequence
<220> FEATURE:
<223> OTHER INFORMATION: F2RL3 Reverse Primer

<400> SEQUENCE: 14
ccagggtgtc actgtcatt                                                    19

<210> SEQ ID NO 15
<211> LENGTH: 19
<212> TYPE: DNA
<213> ORGANISM: Artificial Sequence
<220> FEATURE:
<223> OTHER INFORMATION: G6PC Forward Primer

<400> SEQUENCE: 15
ctgtcaggca ttgctgttg                                                    19

<210> SEQ ID NO 16
```

<211> LENGTH: 21
<212> TYPE: DNA
<213> ORGANISM: Artificial Sequence
<220> FEATURE:
<223> OTHER INFORMATION: G6PC Reverse Primer

<400> SEQUENCE: 16
cttgaggctg gcattataga t                                    21

<210> SEQ ID NO 17
<211> LENGTH: 21
<212> TYPE: DNA
<213> ORGANISM: Artificial Sequence
<220> FEATURE:
<223> OTHER INFORMATION: GFPT2 Forward Primer

<400> SEQUENCE: 17
gaggatatga cgttgacttc c                                    21

<210> SEQ ID NO 18
<211> LENGTH: 23
<212> TYPE: DNA
<213> ORGANISM: Artificial Sequence
<220> FEATURE:
<223> OTHER INFORMATION: GFPT2 Reverse Primer

<400> SEQUENCE: 18
cattccacag ttacagactt ggc                                  23

<210> SEQ ID NO 19
<211> LENGTH: 17
<212> TYPE: DNA
<213> ORGANISM: Artificial Sequence
<220> FEATURE:
<223> OTHER INFORMATION: HIST2H3C Forward Primer

<400> SEQUENCE: 19
cagaagtcca cggagct                                         17

<210> SEQ ID NO 20
<211> LENGTH: 20
<212> TYPE: DNA
<213> ORGANISM: Artificial Sequence
<220> FEATURE:
<223> OTHER INFORMATION: HIST2H3C Reverse Primer

<400> SEQUENCE: 20
caggtccgtc ttaaagtcct                                      20

<210> SEQ ID NO 21
<211> LENGTH: 20
<212> TYPE: DNA
<213> ORGANISM: Artificial Sequence
<220> FEATURE:
<223> OTHER INFORMATION: IGFBP1 Forward Primer

<400> SEQUENCE: 21
cagacagtgt gagacatcca                                      20

<210> SEQ ID NO 22
<211> LENGTH: 20
<212> TYPE: DNA
<213> ORGANISM: Artificial Sequence
<220> FEATURE:
<223> OTHER INFORMATION: IGFBP1 Reverse Primer

<400> SEQUENCE: 22
cctcttccca ttccaagggt                                               20

<210> SEQ ID NO 23
<211> LENGTH: 21
<212> TYPE: DNA
<213> ORGANISM: Artificial Sequence
<220> FEATURE:
<223> OTHER INFORMATION: IL6 Forward Primer

<400> SEQUENCE: 23
gattcaatga ggagacttgc c                                             21

<210> SEQ ID NO 24
<211> LENGTH: 22
<212> TYPE: DNA
<213> ORGANISM: Artificial Sequence
<220> FEATURE:
<223> OTHER INFORMATION: IL6 Reverse Primer

<400> SEQUENCE: 24
ctctcaaatc tgttctggag gt                                            22

<210> SEQ ID NO 25
<211> LENGTH: 21
<212> TYPE: DNA
<213> ORGANISM: Artificial Sequence
<220> FEATURE:
<223> OTHER INFORMATION: KDELR3_v1 Forward Primer

<400> SEQUENCE: 25
cttgtatgtg accaaagtcc t                                             21

<210> SEQ ID NO 26
<211> LENGTH: 20
<212> TYPE: DNA
<213> ORGANISM: Artificial Sequence
<220> FEATURE:
<223> OTHER INFORMATION: KDELR3_v1 Reverse Primer

<400> SEQUENCE: 26
cgtagactgt ctctgaaggt                                               20

<210> SEQ ID NO 27
<211> LENGTH: 20
<212> TYPE: DNA
<213> ORGANISM: Artificial Sequence
<220> FEATURE:
<223> OTHER INFORMATION: KDELR3_v2 Forward Primer

<400> SEQUENCE: 27
gctggagatc ctctggactt                                               20

<210> SEQ ID NO 28
<211> LENGTH: 19
<212> TYPE: DNA
<213> ORGANISM: Artificial Sequence
<220> FEATURE:
<223> OTHER INFORMATION: KDELR3_v2 Reverse Primer

<400> SEQUENCE: 28
gatcagcaag actggagag                                                19

<210> SEQ ID NO 29
<211> LENGTH: 20
<212> TYPE: DNA

```
<213> ORGANISM: Artificial Sequence
<220> FEATURE:
<223> OTHER INFORMATION: KDR Forward Primer

<400> SEQUENCE: 29
ccagatgaca accagacgga                                                   20

<210> SEQ ID NO 30
<211> LENGTH: 19
<212> TYPE: DNA
<213> ORGANISM: Artificial Sequence
<220> FEATURE:
<223> OTHER INFORMATION: KDR Reverse Primer

<400> SEQUENCE: 30
ctgggcacca ttccaccaa                                                    19

<210> SEQ ID NO 31
<211> LENGTH: 20
<212> TYPE: DNA
<213> ORGANISM: Artificial Sequence
<220> FEATURE:
<223> OTHER INFORMATION: KLHL4 Forward Primer

<400> SEQUENCE: 31
ctgtgtggaa cggtatgatc                                                   20

<210> SEQ ID NO 32
<211> LENGTH: 21
<212> TYPE: DNA
<213> ORGANISM: Artificial Sequence
<220> FEATURE:
<223> OTHER INFORMATION: KLHL4 Reverse Primer

<400> SEQUENCE: 32
gaggaacact cagaggtgcc a                                                 21

<210> SEQ ID NO 33
<211> LENGTH: 19
<212> TYPE: DNA
<213> ORGANISM: Artificial Sequence
<220> FEATURE:
<223> OTHER INFORMATION: LAMB3 Forward Primer

<400> SEQUENCE: 33
cagaggcaga ggagctgtt                                                    19

<210> SEQ ID NO 34
<211> LENGTH: 21
<212> TYPE: DNA
<213> ORGANISM: Artificial Sequence
<220> FEATURE:
<223> OTHER INFORMATION: LAMB3 Reverse Primer

<400> SEQUENCE: 34
ccaactccat gtctttcatc c                                                 21

<210> SEQ ID NO 35
<211> LENGTH: 21
<212> TYPE: DNA
<213> ORGANISM: Artificial Sequence
<220> FEATURE:
<223> OTHER INFORMATION: MIOX Forward Primer

<400> SEQUENCE: 35
gtgcgggagt tcaacaagtt c                                                 21
```

<210> SEQ ID NO 36
<211> LENGTH: 17
<212> TYPE: DNA
<213> ORGANISM: Artificial Sequence
<220> FEATURE:
<223> OTHER INFORMATION: MIOX Reverse Primer

<400> SEQUENCE: 36
gtcaatgagc ccctggt                                                  17

<210> SEQ ID NO 37
<211> LENGTH: 20
<212> TYPE: DNA
<213> ORGANISM: Artificial Sequence
<220> FEATURE:
<223> OTHER INFORMATION: MMP9 Forward Primer

<400> SEQUENCE: 37
cagtaccgag agaaagccta                                               20

<210> SEQ ID NO 38
<211> LENGTH: 20
<212> TYPE: DNA
<213> ORGANISM: Artificial Sequence
<220> FEATURE:
<223> OTHER INFORMATION: MMP9 Reverse Primer

<400> SEQUENCE: 38
ccacctggtt caactcactc                                               20

<210> SEQ ID NO 39
<211> LENGTH: 20
<212> TYPE: DNA
<213> ORGANISM: Artificial Sequence
<220> FEATURE:
<223> OTHER INFORMATION: MOCOS Forward Primer

<400> SEQUENCE: 39
ggtgaatgag gcacagtatc                                               20

<210> SEQ ID NO 40
<211> LENGTH: 22
<212> TYPE: DNA
<213> ORGANISM: Artificial Sequence
<220> FEATURE:
<223> OTHER INFORMATION: MOCOS Reverse Primer

<400> SEQUENCE: 40
ctttccattc tcatcactgg tg                                            22

<210> SEQ ID NO 41
<211> LENGTH: 18
<212> TYPE: DNA
<213> ORGANISM: Artificial Sequence
<220> FEATURE:
<223> OTHER INFORMATION: MSI1 Forward Primer

<400> SEQUENCE: 41
tcgagggaca ggctctca                                                 18

<210> SEQ ID NO 42
<211> LENGTH: 17
<212> TYPE: DNA
<213> ORGANISM: Artificial Sequence
<220> FEATURE:

<223> OTHER INFORMATION: MSI1 Reverse Primer

<400> SEQUENCE: 42
tgggagtcga acctgga        17

<210> SEQ ID NO 43
<211> LENGTH: 19
<212> TYPE: DNA
<213> ORGANISM: Artificial Sequence
<220> FEATURE:
<223> OTHER INFORMATION: NUDT5 Forward Primer

<400> SEQUENCE: 43 ccagggqatg gagagtttg       19

<210> SEQ ID NO 44
<211> LENGTH: 20
<212> TYPE: DNA
<213> ORGANISM: Artificial Sequence
<220> FEATURE:
<223> OTHER INFORMATION: NUDT5 Reverse Primer

<400> SEQUENCE: 44
gttcttcagc taccagagca      20

<210> SEQ ID NO 45
<211> LENGTH: 20
<212> TYPE: DNA
<213> ORGANISM: Artificial Sequence
<220> FEATURE:
<223> OTHER INFORMATION: PLG Forward Primer

<400> SEQUENCE: 45
atggctgaaa acaggaagtc      20

<210> SEQ ID NO 46
<211> LENGTH: 24
<212> TYPE: DNA
<213> ORGANISM: Artificial Sequence
<220> FEATURE:
<223> OTHER INFORMATION: PLG Reverse Primer

<400> SEQUENCE: 46
cctccataat cattaggatg agag     24

<210> SEQ ID NO 47
<211> LENGTH: 19
<212> TYPE: DNA
<213> ORGANISM: Artificial Sequence
<220> FEATURE:
<223> OTHER INFORMATION: PRAME Forward Primer

<400> SEQUENCE: 47
ggatcagttg ctcaggcac       19

<210> SEQ ID NO 48
<211> LENGTH: 19
<212> TYPE: DNA
<213> ORGANISM: Artificial Sequence
<220> FEATURE:
<223> OTHER INFORMATION: PRAME Reverse Primer

<400> SEQUENCE: 48
catcacatcc ccttccgaa       19

<210> SEQ ID NO 49
<211> LENGTH: 18
<212> TYPE: DNA
<213> ORGANISM: Artificial Sequence
<220> FEATURE:
<223> OTHER INFORMATION: PTHLH Forward Primer

<400> SEQUENCE: 49
cgcctcaaaa gagctgtg                                                 18

<210> SEQ ID NO 50
<211> LENGTH: 20
<212> TYPE: DNA
<213> ORGANISM: Artificial Sequence
<220> FEATURE:
<223> OTHER INFORMATION: PTHLH Reverse Primer

<400> SEQUENCE: 50
gtgaaggaag aatcgtcgcc                                               20

<210> SEQ ID NO 51
<211> LENGTH: 22
<212> TYPE: DNA
<213> ORGANISM: Artificial Sequence
<220> FEATURE:
<223> OTHER INFORMATION: RARRES1 Forward Primer

<400> SEQUENCE: 51
ggcagtggaa aactaatgat ga                                            22

<210> SEQ ID NO 52
<211> LENGTH: 22
<212> TYPE: DNA
<213> ORGANISM: Artificial Sequence
<220> FEATURE:
<223> OTHER INFORMATION: RARRES1 Reverse Primer

<400> SEQUENCE: 52
cagggaatta tttcctgtgt tg                                            22

<210> SEQ ID NO 53
<211> LENGTH: 21
<212> TYPE: DNA
<213> ORGANISM: Artificial Sequence
<220> FEATURE:
<223> OTHER INFORMATION: RGS7BP Foward Primer

<400> SEQUENCE: 53
tcaagatgac agcagccttc t                                             21

<210> SEQ ID NO 54
<211> LENGTH: 20
<212> TYPE: DNA
<213> ORGANISM: Artificial Sequence
<220> FEATURE:
<223> OTHER INFORMATION: RGS7BP Reverse Primer

<400> SEQUENCE: 54
gaaccttctc ttccgtcttc                                               20

<210> SEQ ID NO 55
<211> LENGTH: 20
<212> TYPE: DNA
<213> ORGANISM: Artificial Sequence
<220> FEATURE:
<223> OTHER INFORMATION: SDPR Forward Primer

<400> SEQUENCE: 55
gctcatcttc caggaggaaa                                                  20

<210> SEQ ID NO 56
<211> LENGTH: 18
<212> TYPE: DNA
<213> ORGANISM: Artificial Sequence
<220> FEATURE:
<223> OTHER INFORMATION: SDPR Reverse Primer

<400> SEQUENCE: 56
ctcctccttc ccttccac                                                    18

<210> SEQ ID NO 57
<211> LENGTH: 20
<212> TYPE: DNA
<213> ORGANISM: Artificial Sequence
<220> FEATURE:
<223> OTHER INFORMATION: SERPINA3 Forward Primer

<400> SEQUENCE: 57
gtctcccagg tggtccataa                                                  20

<210> SEQ ID NO 58
<211> LENGTH: 19
<212> TYPE: DNA
<213> ORGANISM: Artificial Sequence
<220> FEATURE:
<223> OTHER INFORMATION: SERPINA3 Reverse Primer

<400> SEQUENCE: 58
ggagggtgat tttgactgc                                                   19

<210> SEQ ID NO 59
<211> LENGTH: 19
<212> TYPE: DNA
<213> ORGANISM: Artificial Sequence
<220> FEATURE:
<223> OTHER INFORMATION: SLC6A19 Forward Primer

<400> SEQUENCE: 59
gaccctggct acgaggaat                                                   19

<210> SEQ ID NO 60
<211> LENGTH: 19
<212> TYPE: DNA
<213> ORGANISM: Artificial Sequence
<220> FEATURE:
<223> OTHER INFORMATION: SLC6A19 Reverse Primer

<400> SEQUENCE: 60
ccagttcggg taggagatc                                                   19

<210> SEQ ID NO 61
<211> LENGTH: 22
<212> TYPE: DNA
<213> ORGANISM: Artificial Sequence
<220> FEATURE:
<223> OTHER INFORMATION: SLC9A3 Forward Primer

<400> SEQUENCE: 61
ccatcaagga gaaagacttg ga                                               22

<210> SEQ ID NO 62
<211> LENGTH: 19

```
<212> TYPE: DNA
<213> ORGANISM: Artificial Sequence
<220> FEATURE:
<223> OTHER INFORMATION: SLC9A3 Reverse Primer

<400> SEQUENCE: 62
ctagccagga actcgatcc                                                        19

<210> SEQ ID NO 63
<211> LENGTH: 20
<212> TYPE: DNA
<213> ORGANISM: Artificial Sequence
<220> FEATURE:
<223> OTHER INFORMATION: TK1 Forward Primer

<400> SEQUENCE: 63
agaaggaggt cgaggtgatt                                                       20

<210> SEQ ID NO 64
<211> LENGTH: 19
<212> TYPE: DNA
<213> ORGANISM: Artificial Sequence
<220> FEATURE:
<223> OTHER INFORMATION: TK1 Reverse Primer

<400> SEQUENCE: 64
gcctgaggcc ttcttgaag                                                        19

<210> SEQ ID NO 65
<211> LENGTH: 19
<212> TYPE: DNA
<213> ORGANISM: Artificial Sequence
<220> FEATURE:
<223> OTHER INFORMATION: TRPM8 Forward Primer

<400> SEQUENCE: 65
cagaggaaat gaggcatcg                                                        19

<210> SEQ ID NO 66
<211> LENGTH: 26
<212> TYPE: DNA
<213> ORGANISM: Artificial Sequence
<220> FEATURE:
<223> OTHER INFORMATION: TRPM8 Reverse Primer

<400> SEQUENCE: 66
ccttgagatc attaagcttt gtatcc                                                26

<210> SEQ ID NO 67
<211> LENGTH: 19
<212> TYPE: DNA
<213> ORGANISM: Artificial Sequence
<220> FEATURE:
<223> OTHER INFORMATION: TSPAN7 Forward Primer

<400> SEQUENCE: 67
ggaatcgcat tctcccagt                                                        19

<210> SEQ ID NO 68
<211> LENGTH: 23
<212> TYPE: DNA
<213> ORGANISM: Artificial Sequence
<220> FEATURE:
<223> OTHER INFORMATION: TSPAN7 Reverse Primer

<400> SEQUENCE: 68
```
cgtcattctt gaaagacttc tcc                                    23

<210> SEQ ID NO 69
<211> LENGTH: 20
<212> TYPE: DNA
<213> ORGANISM: Artificial Sequence
<220> FEATURE:
<223> OTHER INFORMATION: TUBB3 Forward Primer

<400> SEQUENCE: 69
catctttggt cagagtgggg                                         20

<210> SEQ ID NO 70
<211> LENGTH: 19
<212> TYPE: DNA
<213> ORGANISM: Artificial Sequence
<220> FEATURE:
<223> OTHER INFORMATION: TUBB3 Reverse Primer

<400> SEQUENCE: 70
cacatccagg accgaatcc                                          19

<210> SEQ ID NO 71
<211> LENGTH: 21
<212> TYPE: DNA
<213> ORGANISM: Artificial Sequence
<220> FEATURE:
<223> OTHER INFORMATION: VIPR1 Forward Primer

<400> SEQUENCE: 71
gtacactaca tcatgttcgc c                                       21

<210> SEQ ID NO 72
<211> LENGTH: 20
<212> TYPE: DNA
<213> ORGANISM: Artificial Sequence
<220> FEATURE:
<223> OTHER INFORMATION: VIPR1 Reverse Primer

<400> SEQUENCE: 72
ccacaaaacc ctggaaagac                                         20

<210> SEQ ID NO 73
<211> LENGTH: 19
<212> TYPE: DNA
<213> ORGANISM: Artificial Sequence
<220> FEATURE:
<223> OTHER INFORMATION: WT1 Forward Primer

<400> SEQUENCE: 73
ggaagcacac tggtgagaa                                          19

<210> SEQ ID NO 74
<211> LENGTH: 20
<212> TYPE: DNA
<213> ORGANISM: Artificial Sequence
<220> FEATURE:
<223> OTHER INFORMATION: WT1 Reverse Primer

<400> SEQUENCE: 74
ccttcgttca cagtccttga                                         20

<210> SEQ ID NO 75
<211> LENGTH: 20
<212> TYPE: DNA
<213> ORGANISM: Artificial Sequence
<220> FEATURE:
<223> OTHER INFORMATION: ACTB Forward Primer

<400> SEQUENCE: 75
caagatcatt gctcctcctg                                                   20

<210> SEQ ID NO 76
<211> LENGTH: 19
<212> TYPE: DNA
<213> ORGANISM: Artificial Sequence
<220> FEATURE:
<223> OTHER INFORMATION: ACTB Reverse Primer

<400> SEQUENCE: 76
ccacatctgc tggaaggtg                                                    19

<210> SEQ ID NO 77
<211> LENGTH: 19
<212> TYPE: DNA
<213> ORGANISM: Artificial Sequence
<220> FEATURE:
<223> OTHER INFORMATION: RPL13A Forward Primer

<400> SEQUENCE: 77
cacttgggga cagcatgag                                                    19

<210> SEQ ID NO 78
<211> LENGTH: 20
<212> TYPE: DNA
<213> ORGANISM: Artificial Sequence
<220> FEATURE:
<223> OTHER INFORMATION: RPL13A Reverse Primer

<400> SEQUENCE: 78
gtaacccctt ggttgtgcat                                                   20

<210> SEQ ID NO 79
<211> LENGTH: 19
<212> TYPE: DNA
<213> ORGANISM: Artificial Sequence
<220> FEATURE:
<223> OTHER INFORMATION: RPL9 Forward Primer

<400> SEQUENCE: 79
cggatgagac caggtgttg                                                    19

<210> SEQ ID NO 80
<211> LENGTH: 22
<212> TYPE: DNA
<213> ORGANISM: Artificial Sequence
<220> FEATURE:
<223> OTHER INFORMATION: RPL9 Reverse Primer

<400> SEQUENCE: 80
caagctcaat gtcatttcct tc                                                22

<210> SEQ ID NO 81
<211> LENGTH: 19
<212> TYPE: DNA
<213> ORGANISM: Artificial Sequence
<220> FEATURE:
<223> OTHER INFORMATION: RPS29 Forward Primer

<400> SEQUENCE: 81
gctcttgtcg tgtctgttc                                                    19

```
<210> SEQ ID NO 82
<211> LENGTH: 19
<212> TYPE: DNA
<213> ORGANISM: Artificial Sequence
<220> FEATURE:
<223> OTHER INFORMATION: RPS29 Reverse Primer

<400> SEQUENCE: 82
cgtactgacg gaaacactg                                                19
```

METHOD OF TREATING A PATIENT HAVING RENAL CANCER

CROSS-REFERENCE TO RELATED APPLICATIONS

This application is a National Stage application of PCT/SG2014/000446, filed Sep. 17, 2014, which claims priority from Singapore Application No. 2013070149, filed Sep. 17, 2013, each of which are hereby incorporated by reference in their entireties.

SEQUENCE LISTING

In accordance with 37 CFR § 1.52(e)(5), a Sequence Listing in the form of a text file (entitled "Sequence Listing.txt," created Mar. 17, 2016 and 16 KB in size) is incorporated herein by reference in its entirety.

FIELD OF THE INVENTION

The present invention relates to assays for clear-cell renal cell carcinomas and in particular, assays for prognosis and drug response prediction in clear-cell renal cell carcinomas. More specifically, the present invention relates to multigene assays using formalin-fixed paraffin embedded samples. Kits of reagents are also provided.

BACKGROUND OF THE INVENTION

Clear-cell renal carcinomas (ccRCCs) are the most common histologic variant of renal cancers, accounting for about 80% of these tumours. About 30% of localized ccRCCs recur as incurable metastatic disease after surgery with intent to cure. Currently, tumour stage at presentation is the most reliable predictor of clinical course of disease after surgery. However, there remains significant disparity within the same staging group and clinical outcome. Other variables that influence outcome include Fuhrman grade, tumour size, necrosis and performance status. Despite an abundance of models for patient stratification, it remains challenging to predict metastasis of ccRCCs. Further, using currently available staging systems many patients are assigned to intermediate-risk categories making stratification to treatment groups challenging.

ccRCCs in advanced stages are highly refractory to chemotherapy, and the standard of care for several years was immunotherapy, despite its limited efficacy with response rates of 5 to 20%. With a better understanding of the molecular biology behind development of ccRCC, a number of molecular-targeted therapies have come to dominate treatment strategies. For example, inhibition of tumour neoangiogenesis by inhibition of vascular endothelial growth factor (VEGF) or mammalian target of rapamycin (mTOR) pathways have demonstrated clinical benefit. Despite these advances, only 15-25% of patients with metastatic disease experience benefit from currently available therapies, with overall median survival remaining dismally low at less than one year.

Currently treatment decisions are made based on clinical criteria, and prognostic models for survival in the metastatic setting are available for patients treated with tyrosine kinase inhibitors (TKI). However, most algorithms are not predictive of response to therapy and validated molecular markers that can identify patients likely to benefit from therapy are lacking. Patients stratified into similar risk categories by one of the currently available prognostic algorithms can go on to experience divergent outcomes when administered targeted therapy, undermining the efficacy of such therapy.

There is therefore a need to provide a method for predicting clinical outcomes of ccRCCs that overcomes, or at least ameliorates, one or more of the disadvantages described above.

SUMMARY OF THE INVENTION

In a first aspect there is provided, a method of making a prognosis as to whether a patient having renal cancer is likely to survive in a tumour tissue sample obtained from the patient comprising: determining the level of expression for each marker of a panel of markers, wherein the panel comprises at least one housekeeping gene selected from the group consisting of ACTB, RPL13A, RPL9, and RPS29 and any combinations thereof; and at least one prognostic gene selected from the group consisting of CXCL5, EFNA5, EMCN, G6PC, GFPT2, HIST2H3C, IGFBP1, LAMB3, MMP9, MOCOS, PLG, PRAME, RARRES1, SDPR, SLC6A19, TK1, KDELR3 and TSPAN7 and any combinations thereof; determining whether an expression parameter for each marker in the tumour tissue sample is achieved by comparing the level of expression of each marker with a predetermined reference level associated with each marker; determining the differential expression of each marker in the tumour tissue sample based on the expression parameter for each marker to provide a prognosis for renal cancer.

In a second aspect there is provided, a method for predicting responsiveness to an anti-renal cancer treatment in a patient having or at risk of developing renal cancer in a tumour tissue sample obtained from the patient comprising: determining the level of expression for each marker of a panel of markers, wherein the panel comprises at least one housekeeping gene selected from the group consisting of ACTB, RPL13A, RPL9, and RPS29 and any combinations thereof; and at least one prognostic gene selected from the group consisting of CXCL5, EFNA5, EMCN, G6PC, GFPT2, HIST2H3C, IGFBP1, LAMB5, MMP9, MOCOS, PLG, PRAME, RARRES1, SDPR, SLC6A19, TK1, KDELR3 and TSPAN7 and any combinations thereof; determining whether an expression parameter for each marker in the tumour tissue sample is achieved by comparing the level of expression of each marker with a predetermined reference level associated with each marker; wherein differential expression of each marker in the tumour tissue sample based on the expression parameter for each marker is indicative of the responsiveness of the patient to the anti-renal cancer treatment.

A kit comprising: at least one reagent to determine the level of expression for each marker of a panel of markers in a tissue tumour sample, wherein the panel comprises at least one housekeeping gene selected from the group consisting of ACTB, RPL13A, RPL9, and RPS29 and any combinations thereof; and at least one prognostic gene selected from the group consisting of CXCL5, EFNA5, EMCN, G6PC, GFPT2, HIST2H3C, IGFBP1, LAMB3, MMP9, MOCOS, PLG, PRAME, RARRES1, SDPR, SLC6A19, TK1, KDELR3 and TSPAN7 and any combinations thereof.

A kit comprising: at least one reagent to determine the level of expression for each marker of a panel of markers in a tissue tumour sample, wherein the panel comprises at least one housekeeping gene selected from the group consisting of ACTB, RPL13A, RPL9, and RPS29 and any combinations thereof; and at least one prognostic gene selected from the group consisting of CXCL5, EFNA5, EMCN, G6PC, GFPT2, HIST2H3C, IGFBP1, LAMB3, MMP9, MOCOS, PLG, PRAME, RARRES1, SDPR, SLC6A19, TK1, KDELR3 and TSPAN7 and any combinations thereof.

Definitions

The terms "biological material" or "biological sample" as used herein refers to any material or sample, which includes an analyte as defined herein. Such samples may, for example, include samples derived from or comprising stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid-harvested from a site of an immune response, fluid harvested from a pooled collection site, bronchial lavage, urine, biopsy material, e.g. from all suitable organs, e.g. the lung, the muscle, brain, liver, skin, pancreas, stomach, etc., a nucleated cell sample, a fluid associated with a mucosal surface, hair, or skin.

The invention illustratively described herein may suitably be practiced in the absence of any element or elements, limitation or limitations, not specifically disclosed herein. Thus, for example, the terms "comprising"; "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

The invention will be better understood with reference to the detailed description when considered in conjunction with the non-limiting examples and the accompanying drawings, in which:

FIG. 1A shows the cluster dendrogram of 55 ccRCC samples grouped by expression of 3740 genes 0.10 measured by DASL analysis. Two main groups are formed (n1=43 and n2=12) denoted by solid and dashed lines under the dendogram. FIG. 1B shows Kaplan-Meier curves of disease-specific survival for two prognostic subtypes generated by hierarchical clustering. Survival in the good prognosis group is significantly better than in the poor prognosis group (p=0.0185 by log-rank test).

FIG. 2 shows distribution of tumour grade, stage and size in prognostic subtypes identified by unsupervised hierarchical clustering of 55 ccRCCs by gene expression data. Good prognosis and poor prognosis subtypes are designated by solid and dashed lines below dendogram.

FIG. 3A to 3D. Relatively stable expression of four normalization genes in 55 ccRCCS measured by DASL assay. FIG. 3A. β-actin. FIG. 3B. RPL9. FIG. 3C. RPL13A. FIG. 3D. RPS29. The y-axes represent expression and x-axes corresponds to the samples index number of 55 ccRCCs.

FIG. 4 shows expression was measured by qPCR and plotted with respect to prognostic subtypes illustrating expression patterns in prognosis subtypes 1 and 2 highlighted by solid and dashed lines. Prognosis subtypes are derived from the screening cohort of 55 ccRCCs analyzed on DASL platform. Black cells represent low expression and white cells represent high expression.

FIG. 5 shows prognostic scores for 214 ccRCCs based on qPCR gene expression were calculated and samples assigned to low- or high-scoring groups (cut-off at 0.6). Survival analysis by Kaplan-Meier method shows significant difference in disease-specific survival between low- and high-scoring groups corresponding to poor and good prognosis ccRCCs respectively.

FIG. 6A to 6C show survival analysis by Kaplan-Meier method for ccRCC patients classified into good- and poor-prognosis subtypes based on expression of eight genes. A difference is observed in cancer specific survival between two prognosis subtypes. FIG. 6A shows prognostic subtype assignment for Singapore General Hospital (SGH)-224 validation cohort (n=224) based on quantitative polymerase chain reaction gene expression measurement in formalin-fixed paraffin-embedded tumours. FIG. 6B shows prognostic subtype assignment for the Cancer Genome Atlas (TCGA)-419 validation cohort (n=419) by classification algorithm applied to RNA-sequencing expression data. It should be noted that the TCGA dataset is enriched in patients with higher-grade disease with an overall poor survival outlook, with only five samples classified as histologic grade 1 tumours. FIG. 6C shows prognostic subtype assignment for VARI-174 validation cohort based on Affymetrix microarray expression data (Affymetrix, Santa Clara, Calif., USA).

DETAILED DESCRIPTION OF THE PRESENT INVENTION

Figure 1:
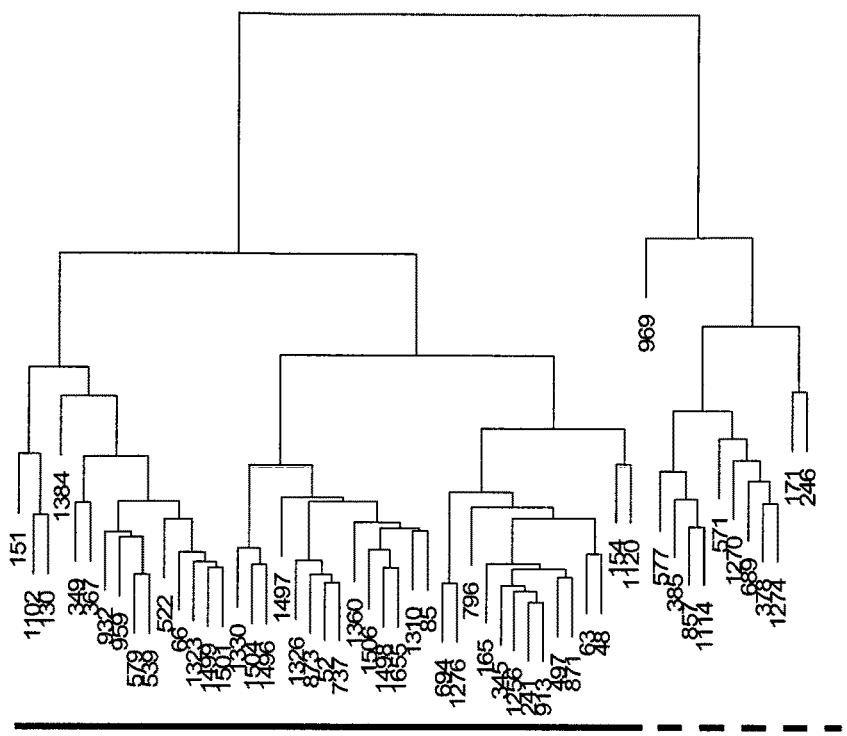
FIGS. 1A and 1B. Unsupervised Hierarchical Clustering Analysis of 55 ccRCCs based on DASL expression data identifies two prognostic subtypes.
Figure 1:
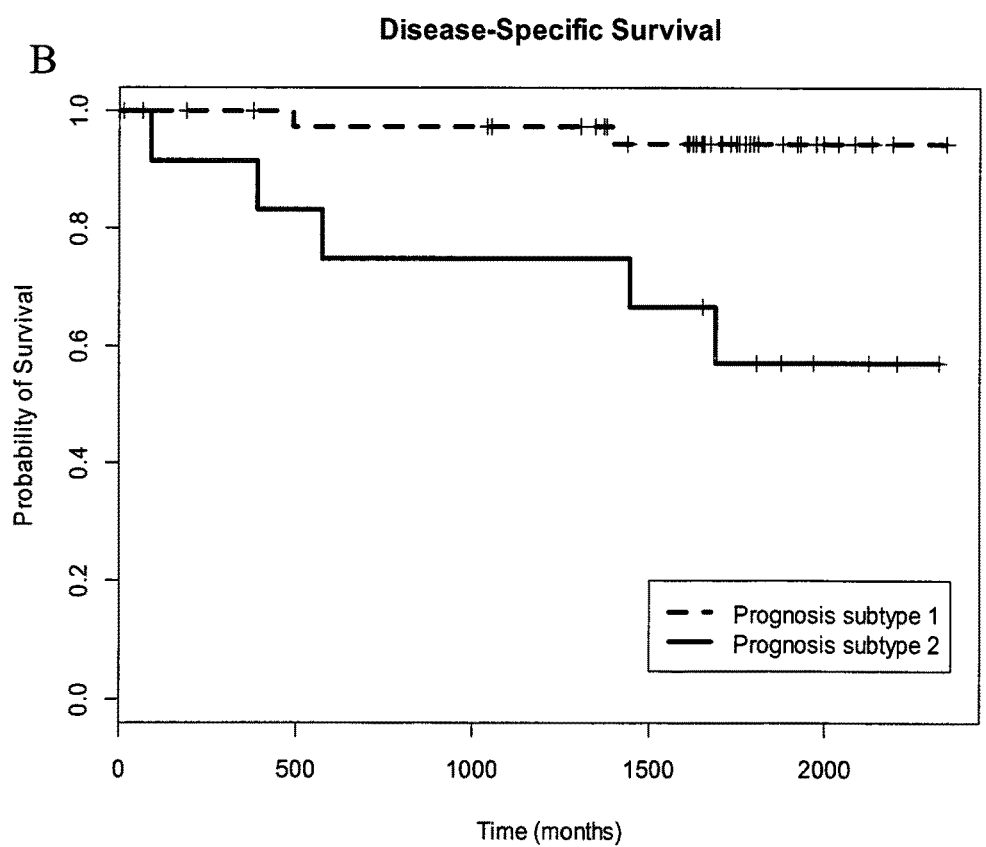

In a first aspect the present invention refers to a method of making a prognosis as to whether a patient having renal cancer is likely to survive in a tumour tissue sample obtained from the patient. The method may comprise: determining the level of expression for each marker of a panel of markers, wherein the panel comprises at least one housekeeping gene selected from the group consisting of ACTB, RPL13A, RPL9, and RPS29 and any combinations thereof; and at least one prognostic gene selected from the group consisting of CXCL5, EFNA5, EMCN, G6PC, GFPT2, HIST2H3C, IGFBP1, LAMB3, MMP9, MOCOS, PLG, PRAME, RARRES1, SDPR, SLC6A19, TK1, KDELR3 and TSPAN7 and any combinations thereof; determining whether an expression parameter for each marker in the tumour tissue sample is achieved by comparing the level of expression of each marker with a predetermined reference level associated with each marker; determining the differential expression of each marker in the tumour tissue sample based on the expression parameter for each marker to provide a prognosis for renal cancer.

The prognostic gene may be selected from the group consisting of CXCL5, LAMB3, MMP9, PRAME, RARRES1, PLG, SLC6A19, EFNA5, IGFBP1 and EMCN and any combinations thereof.

In one embodiment, the renal cancer may be clear cell renal cell carcinoma (ccRCC) or a mixture of renal tumours comprising ccRCC.

In one embodiment, the patient may suffer from ccRCC or wherein the patient suffers from ccRCC and undergoes anti-cancer treatment. The likelihood of survival may correlate with a decrease in the likelihood of metastasis, disease recurrence or early death.

The tumour tissue sample may be obtained from tissue selected from the group consisting of frozen tissue, tissue biopsies, circulating tumor cells, bodily fluids or other biological sample.

In one embodiment, the bodily fluids are selected from the group consisting of ascites, effusions, cerebrospinal and urine.

The patient may be undergoing anti-cancer treatment. The anti-cancer treatment may be selected from the group consisting of a chemotherapeutic treatment, a surgical treatment, a treatment with radiation therapy, immunotherapy, targeted therapy, small molecule therapeutics or any combination thereof. In some embodiments then chemotherapeutic treatment may comprise treatment with a protein kinase inhibitor, receptor tyrosine kinase inhibitor, antimetabolite, platinum complex, spindle poison, DNA crosslinking drug and alkylating agent, bleomycin, antibiotic, and topoisomerase inhibitor or combinations thereof.

The receptor tyrosine kinase inhibitor may be selected from the group consisting of sunitinib, pazopanib, axitinib, sorafenib or combinations thereof.

In some embodiments the protein kinase inhibitor may be temsirolimus or everolimus.

The targeted therapy may comprise anti-tumour antibodies such as bevacizumab, interferon and combinations thereof.

The immunotherapy may be interferon, high-dose-interleukin 2 or combinations thereof.

The small molecule therapeutic may comprise tivozantinib.

The patient may be a mammal or a human. In some embodiments, the human may be an ethnic Asian, or an ethnic Caucasian, or an ethnic African.

The predetermined reference level may be determined based on the expression of the at least one housekeeping gene. In some embodiments, the determining of whether or not the biomarkers are differentially expressed in the sample further comprises normalizing the levels of expression of the markers to the at least one housekeeping gene selected from the group consisting of ACTB, RPL13A, RPL9, and RPS29 and any combinations thereof.

In some embodiments, the levels of expression of the markers may be normalized against the geometric mean $C_T$ value of the at least one housekeeping gene.

In some embodiments, an increase in the expression parameter of prognostic genes selected from the group consisting of EMCN, G6PC, PLG, SDPR, SLC6A19 and TSPAN7 may indicate an increased chance of survival. In some embodiments, a decrease or absence in the expression parameter of prognostic genes selected from the group consisting of G6PC, PLG, SDPR, SLC6A19 and TSPAN7 may indicate a decreased chance of survival.

An increase in the expression parameter of prognostic genes selected from the group consisting of CXCL5, EFNA5, GFPT2, HIST2H3C, IGFBP1, LAMB3, MMP9, MOCOS, PRAME, RARRES1 and TK1 may indicate a decreased chance of survival.

A decrease or absence in the expression parameter of prognostic genes selected from the group consisting of GFPT2 and LAMB3 may indicate an increased chance of survival. In some embodiments, the prognosis may be determined by a multivariate algorithm. The multivariate algorithm may be multivariate logistic correlation analysis or linear discriminant analysis (LDA).

The multivariate algorithm may use a class prediction approach.

In a second aspect the present invention refers to a method for predicting responsiveness to an anti-renal cancer treatment in a patient having or at risk of developing renal cancer in a tumour tissue sample obtained from the patient comprising: determining the level of expression for each marker of a panel of markers, wherein the panel comprises at least one housekeeping gene selected from the group consisting of ACTB, RPL13A, RPL9, and RPS29 and any combinations thereof; and at least one prognostic gene selected from the group consisting of CXCL5, EFNA5, EMCN, G6PC, GFPT2, HIST2H3C, IGFBP1, LAMB3, MMP9, MOCOS, PLG, PRAME, RARRES1, SDPR, SLC6A19, TK1, KDELR3 and TSPAN7 and any combinations thereof; determining whether an expression parameter for each marker in the tumour tissue sample is achieved by comparing the level of expression of each marker with a predetermined reference level associated with each marker; wherein differential expression of each marker in the tumour tissue sample based on the expression parameter for each marker is indicative of the responsiveness of the patient to the anti-renal cancer treatment.

The prognostic gene in may be selected from the group consisting of CXCL5, LAMB3, MMP9, PRAME, RARRES1, PLG, SLC6A19, EFNA5, IGFBP1 and EMCN and any combinations thereof.

In some embodiments, an increase in the expression parameter of prognostic genes selected from the group consisting of EMCN, G6PC, PLG, SDPR, SLC6A19 and TSPAN7 may indicate an increased responsiveness to the treatment and an increased chance of survival.

In some embodiments, a decrease or absence in the expression parameter of prognostic genes selected from the group consisting of EMCN, G6PC, PLG, SDPR, SLC6A19 and TSPAN7 may indicate a decreased responsiveness to the treatment and a decreased chance of survival.

In one embodiment, an increase in the expression parameter of prognostic genes selected from the group consisting of CXCL5, EFNA5, GFPT2, HIST2H3C, IGFBP1, LAMB3, MMP9, MOCOS, PRAME, RARRES1 and TK1 may indicate a decreased responsiveness to the treatment and a decreased chance of survival.

In one embodiment a, decrease or absence in the expression parameter of prognostic genes selected from the group consisting of CXCL5, EFNA5, GFPT2, HIST2H3C, IGFBP1, LAMB3, MMP9, MOCOS, PRAME, RARRES1 and TK1 may indicate an increased responsiveness to the treatment and an increased chance of survival.

In some embodiments, the renal cancer is a clear cell renal cell carcinoma (ccRCC).

In one embodiment, the step of determining the level of expression of each marker may comprise: contacting a nucleic acid sequence obtained or derived from said sample with at least one primer and/or at least one probe for amplification of a sequence of the marker; amplifying said nucleic acid sequence using said at least one primer or probe with a polymerase enzyme; detecting the level of expression of the marker in said sample.

In one embodiment, the amplification step may be performed by polymerase chain reaction (PCR).

In a second aspect the present invention refers to a kit comprising: at least one reagent to determine the level of expression for each marker of a panel of markers in a tissue tumour sample, wherein the panel comprises at least one housekeeping gene selected from the group consisting of ACTB, RPL13A, RPL9, and RPS29 and any combinations thereof; and at least one prognostic gene selected from the group consisting of CXCL5, EFNA5, EMCN, G6PC, GFPT2, HIST2H3C, IGFBP1, LAMB3, MMP9, MOCOS, PLG, PRAME, RARRES1, SDPR, SLC6A19, TK1, KDELR3 and TSPAN7 and any combinations thereof.

In one embodiment, the prognostic gene may be selected from the group consisting of CXCL5, LAMB3, MMP9, PRAME, RARRES1, PLG, SLC6A19, EFNA5, IGFBP1 and EMCN and any combinations thereof.

In one embodiment, the at least one reagent may comprise at least one primer and/or at least one probe for amplification of a sequence comprising the marker.

EXAMPLES

Example 1

Development of a Prognostic Assay for Clear Cell Renal Cell Carcinoma (ccRCC)

Methods

Study Population

The study was done in a retrospective manner with patient cohort that included 279 ccRCC patients who underwent resection for clear-cell renal cell carcinoma at National Cancer Centre, Singapore between 1999 and 2012. All patients had histologically confirmed ccRCCs for which formalin-fixed paraffin-embedded (FFPE) primary or metastatic tumour blocks were available. Fifty-five FFPE samples were used for Illumina's Whole Genome DASL analysis. For qPCR analysis 214 FFPE samples were used. This group included 48 patients with metastatic ccRCCs treated with anti-VEGF targeted treatment (sunitinib or pazopanib) as first-, second or third-line therapy. The patient database included patients' baseline pathological features and disease outcome data including date of death or last follow-up. Disease-specific survival time was calculated from date of first diagnosis. All patients provided written informed consent, and the study was approved by SingHealth Institutional Review Board.

RNA Extraction, cDNA Synthesis and Quantitative PCR

FFPE blocks were sectioned into 4-μm sections, stained with hematoxylin-eosin for confirmation of histological diagnosis and tumour tissue content (>70%). Following deparaffinization of 3-6 FFPE sections per sample, macrodissection was performed with a sterile single-use scalpel to remove nontumour elements and RNA was extracted using Qiagen's RNeasy FFPE Kit. Integrity of RNA samples was assessed by verifying amplification of housekeeping gene RPL13A using Power SYBR Green RNA-to-CT, 1-Step kit (Applied Biosystems) with 100 ng of RNA template. Samples that had cycle threshold (Ct) value for RPL13A below 29, were used for Illumina Whole genome-DASL expression analysis or for subsequent conversion to complementary DNA. All DASL (cDNA-mediated Annealing, Selection, extension, and Ligation) assays were performed in Biopolis Shared Facilities, A*STAR, Singapore.

For selected genes, primers were designed for amplicons of size 55-90 bp, with at least primer spanning exon-exon boundaries. For qPCR, 1 μg extracted. RNA was reverse transcribed with random hexamer primers using High Capacity cDNA Reverse Transcription Kit (Applied Biosystems). Relative expression of each target gene was measured by real-time qPCR with Power SYBR Green Master Mix (Applied Biosystems) on a Bio Rad CFX96 machine. cDNA was diluted four-fold and 1 μl of the diluted cDNA was used as template in a 10 μl reaction with primers at a final concentration of 200 nM. Products were checked for specificity of amplification with melt curve and positive and negative controls were run for each plate.

Identification of Prognostic Genes

Quantile-normalized gene expression data for 55 ccRCCs analyzed by Illumina's DASL Assay using HumanHT-12 v4 BeadChip (24,526 features) was obtained using Genomestudio. Data was further analyzed with R 2.13.1 using packages Genefilter, Survival and siggenes. Data was first filtered to include probes that were present in at least one sample defined by detection p-value <0.05 (19,303 features). Further, genes with expression values greater than 3000 in at least one sample and with covariance greater than 0.75 were selected (3740 features) as reliably expressed features with reasonably high variation in expression among 55 samples. Unsupervised hierarchical clustering (Ward clustering) of samples by the selected features was done and resulting clusters were cut at the highest level to generate two main expression subgroups. Significance analysis of microarrays (SAM) was applied to select features that were significantly differentially expressed between the two subgroups ($p<0.05$).

Quantitative PCR Data Analysis

Expression data for 18 genes for all FFPE RNA samples was collected as cycle threshold (Ct) values. Expression was normalized by subtracting Ct values from the geometric average of Ct values for four housekeeping genes. When Ct exceeded 36, expression was not subject to data transformation and deemed to be of value zero. Following normalization, a value of +14.72 was added to the delta Ct values to scale negative values to start from 0 and to fall on a positive scale, where a 1-unit increase reflects a doubling of RNA. These transformed delta Ct values were used for further analysis.

Statistical Analysis

To determine correlation of expression by DASL and qPCR, transformed qPCR data was converted to a linear scale by the function $2^{\Delta\Delta Ct}$. Linear correlation between the linear qPCR expression data and DASL expression values in 55 samples was determined by Pearson's product-moment correlation. The ten most significantly correlated genes representing a successful translation for measuring expression on the qPCR platform were selected to generate a model for a prognostic score with which to correlate clinical outcomes.

Expression values from qPCR for 10 genes were used to generate a model using multivariate logistic regression analysis for the dichotomous outcome of good or poor prognosis classification from the original prognosis groups generated by unsupervised hierarchical clustering of DASL expression data. The intercept and coefficients for each of 10 genes were generated using this multivariate analysis. The cut-off score to classify prognosis groups was determined as the score at which misclassification of 55 ccRCC samples using the prognostic score, with respect to their original class assignment was minimized (9%).

Prognostic scores for 214 FFPE RNA samples were determined from expression values of 10 genes according to the derived algorithm. Based on the pre-determined cut-off, samples were stratified into low- and high-scoring groups corresponding to poor and good prognosis categories respectively. The distribution of disease-specific survival was estimated by the Kaplan-Meier method with log-rank test to assess the association of the prognosis category with primary end-point of disease-specific mortality. Other clinical covariates including age, tumour stage and tumour grade were compared to outcome using univariate and multivariate Cox proportional hazards modeling. Wald and likelihood ratio tests were done for multivariate modeling to assess statistical significance. Cox model was also used to estimate hazard ratios and 95% CI for prognosis category. A subset of 34 samples corresponding to patients that underwent TKI therapy with evaluable clinical response data, were stratified into prognosis groups. Objective response was classified as partial response, stable disease, progressive disease or mixed response. The partial response and stable disease categories were classified as responders and progressive disease and mixed response categories were classified as non-responders. The significance of association between prognosis groups and response outcome was measured using Fisher's exact method. A logistic regression analysis was used to assess the association between prognostic score as a continuous score and response to TKI as a categorical variable.

Results

Material from 55 patients was analyzed in the screening cohort initially for whole-genome expression profiling and subsequent selection and confirmation of prognostic genes, and material from 214 patients was analyzed to validate the performance of prognostic genes. Baseline characteristics of patients in the initial screening group are described in Table 1.

TABLE 1

Characteristics of patients in initial screening group used for DASL study

| | | |
|---|---|---|
| Number of samples | | 55 |
| Age | Range | 32-81 |
| | Median | 59 |
| Gender-n (%) | Male | 43 (78%) |
| | Female | 12 (22%) |
| TNM stage | I | 33 (60%) |
| | II | 2 (3.6%) |
| | III | 14 (25.5%) |
| | IV | 6 (10.9%) |
| Tumour T stage | 1 | 33 (60%) |
| | 2 | 3 (5.5%) |
| | 3 | 18 (32.7%) |
| | 4 | 1 (1.8%) |

TABLE 1-continued

Characteristics of patients in initial screening group used for DASL study

| | | |
|---|---|---|
| Tumour M stage | 0 | 41 (74.5%) |
| | 1 | 6 (10.9%) |
| | X | 8 (14.5%) |
| Tumour Grade | 1 | 9 (16.3%) |
| | 2 | 29 (52.7%) |
| | 3 | 9 (16.4%) |
| | 4 | 8 (14.5%) |
| Primary tumour size | Range | 1.9-16 |
| | Median | 5 |
| | <4 | 16 (29%) |
| | 4 to 7 | 26 (47%) |
| | >7 | 13 (24%) |
| | Unknown | |
| ECOS PS | 0 | 37 (67.2%) |
| | 1 | 13 (23.6%) |
| | 2 | 0 (0%) |
| | Unknown | 5 (9%) |
| Follow-up duration (yr) | Range | 0.036-6.42 |
| | Mean | 4.19 |
| Patient Status | Deaths (cancer-related) | 7 (12.7%) |
| | Deaths (other causes) | 2 (3.6%) |
| | Alive with disease | 2 (3.6%) |
| | No evidence of disease | 44 (80%) |
| Post-nephrectomy treatment | Sunitinib | 4 (7.2%) |
| | Pazopanib | 1 (1.8%) |
| | Interferon | 1 (1.8%) |
| | 5FU + PTK/ZK | 1 (1.8%) |

2 patients without nephrectomy-1 definite metastasis.

All patients in the screening group underwent nephrectomy for primary tumour, except two patients who were operated on metastatic tumours in the lungs. Following retrieval of paraffin blocks for primary or metastatic tissue, RNA was extracted from FFPE sections and integrity of RNA validated before whole-genome expression profiling was done for 55 ccRCC. Characteristics of patients from the validation group are described in Table 2. Eleven patients did not undergo nephrectomy and tissue was obtained from biopsies or metastatic tissue.

TABLE 2

Characteristics of patients in confirmation group

| | | |
|---|---|---|
| Number of samples | | 224 |
| Age | Range | 29-91 |
| | Median | 56.5 |
| Gender | Male | 152 (68%) |
| | Female | 72 (32%) |
| TNM stage | I | 106 (47.3%) |
| | II | 26 (11.6%) |
| | III | 55 (24.6%) |
| | IV | 36 (16.1%) |
| | Unknown | 1 (0.5%) |
| Tumour T stage | 1 | 109 (50.9%) |
| | 2 | 33 (15.4%) |
| | 3 | 67 (31.3%) |
| | 4 | 1 (0.5%) |
| | X | 3 (1.4%) |
| | NA | 1 (0.5%) |
| Tumour M stage | 0 | 181 (84.5%) |
| | 1 | 32 (15%) |
| | Unknown | 1 (0.5%) |
| Tumour Grade | 1 | 22 (10.3%) |
| | 2 | 113 (52%) |
| | 3 | 63 (27%) |
| | 4 | 25 (10.3%) |

TABLE 2-continued

Characteristics of patients in confirmation group

| | | |
|---|---|---|
| Primary tumour size | Range | 1.5-25 |
| | Median | 5.5 |
| ECOS PS | 0 | 126 (56.2%) |
| | 1 | 47 (21%) |
| | 2 | 3 (1.4%) |
| | Unknown | 48 (21.4%) |
| Follow-up duration (yr) | Range | 0.049-12.19 |
| | Mean | 5.54 |
| Patient Status | Deaths (cancer-related) | 49 (21.9%%) |
| | Deaths (other causes) | 14 (6.3%) |
| | Alive with disease | 27 (12%) |
| | No evidence of disease | 134 (59.8%) |

11 patients without nephrectomy.

Figure 2:
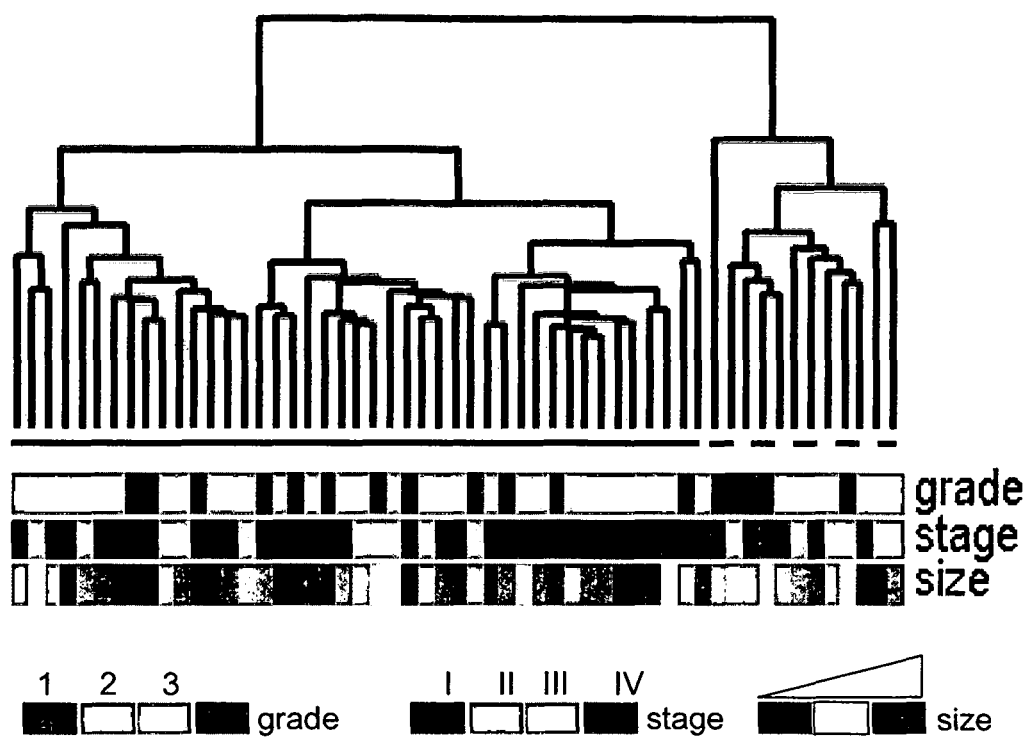
FIG. 2. Correlation of gene expression subgroups to clinicopathological features.

In order to identify biologically relevant subtypes of ccRCC based on gene expression profiling, whole-genome expression data for the screening group of 55 ccRCC was processed to derive a gene set that is reliably detectable (expressed) with elements of this set retaining reasonably high variation of expression among the samples. As RNA from FFPE material is of a highly degraded nature, preprocessing of data was done to only include features that had significant expression (p<0.05) as defined by. Illumina detection platform. A set of 3740 features which had significant expression in at least one sample (expression values more than 3000) and a coefficient of variation greater than 0.75, was used for performing unsupervised hierarchical clustering of 55 ccRCCs. Samples were partitioned into two main groups based on differential expression of these 3740 features (FIG. 1A). Kaplan-Meier analysis showed that the two main groups of ccRCC defined by unsupervised hierarchical clustering differed in disease-specific survival (p=0.00185 by log-rank test) (FIG. 1B). These two subgroups were then defined as biologically-defined prognostic subtypes that can be distilled based on their gene expression patterns. Prognostic subtypes were also associated with other relevant clinicopathologic features such as tumour grade, stage and tumour size (FIG. 2).

Having delineated two main biologically-defined prognostic subtypes, genes that were most significantly differentially expressed between these two subtypes, and expression levels of which could potentially be used to accurately classify ccRCCs were identified. To achieve this, significance analysis of microarrays (SAM) analysis was applied to the highest level of the resulting clustering dendrogram (FIG. 1A), and the most discriminatory genes defining the two subtypes were identified. This analysis produced 220 genes as the most differentially expressed between prognostic subtypes (q<0.05). This set of genes represents potential prognostic genes and are listed in Table 3. The ideal prognostic gene should have a large fold-difference between prognostic groups but limited variation within the same prognostic group. Also, the prognostic gene should be amenable to accurate reproducible measurement by an independent method such as qPCR.

TABLE 3

List of genes significantly differentially expressed between Prognosis subtypes 1 and 2.

| Gene | q. value | R. fold | Prognosis Subtype 1 Mean | Prognosis Subtype 1 SD | Prognosis Subtype 2 Mean | Prognosis Subtype 2 SD |
|---|---|---|---|---|---|---|
| NME1 | 0.00 | 1.86 | 4115.43 | 1416.31 | 7308.75 | 1247.38 |
| TSPAN7 | 0.00 | 0.15 | 3354.05 | 1756.40 | 559.59 | 412.96 |
| PLG | 0.00 | 0.08 | 4141.75 | 6073.62 | 65.42 | 4.21 |
| F12 | 0.01 | 3.68 | 1712.15 | 1060.05 | 5794.40 | 2836.39 |
| TUBB3 | 0.01 | 5.46 | 1661.67 | 1721.87 | 5592.52 | 2669.45 |
| KDELR3 | 0.01 | 4.24 | 1009.97 | 1294.46 | 2802.80 | 1147.52 |
| TUBA1C | 0.01 | 1.38 | 29840.58 | 4981.53 | 41013.67 | 5110.15 |
| CTHRC1 | 0.01 | 4.27 | 2791.22 | 1957.13 | 10061.91 | 5098.79 |
| PPAP2A | 0.01 | 0.65 | 15673.18 | 2879.62 | 10147.16 | 1896.57 |
| VIPR1 | 0.01 | 0.12 | 27517.56 | 16607.77 | 3697.29 | 2695.32 |
| RAG1AP1 | 0.01 | 1.23 | 7458.21 | 961.35 | 9093.07 | 599.98 |
| SEC61G | 0.01 | 1.53 | 13658.87 | 3362.98 | 20565.09 | 3389.91 |
| C15orf58 | 0.01 | 2.01 | 2693.30 | 1167.46 | 4974.76 | 1099.97 |
| FKBP10 | 0.01 | 2.07 | 4606.42 | 2337.31 | 8518.46 | 1914.65 |
| ANKRD56 | 0.01 | 0.33 | 386.91 | 456.28 | 71.59 | 7.79 |
| SLC7A5 | 0.01 | 2.85 | 12127.31 | 7564.27 | 26289.58 | 6651.07 |
| TK1 | 0.01 | 5.71 | 2332.11 | 2041.67 | 7540.38 | 3417.20 |
| FATE1 | 0.01 | 0.34 | 470.08 | 502.89 | 102.66 | 27.37 |
| CCT3 | 0.01 | 1.53 | 4860.83 | 1587.98 | 7230.99 | 1248.00 |
| RGS7BP | 0.01 | 0.09 | 2723.24 | 2375.56 | 379.83 | 877.70 |
| MOCOS | 0.01 | 11.35 | 334.56 | 846.20 | 2690.46 | 2250.93 |
| MAZ | 0.01 | 1.47 | 3572.83 | 960.98 | 5133.94 | 857.64 |
| PYGB | 0.01 | 3.16 | 1047.23 | 754.87 | 2636.35 | 1121.14 |
| EFNA5 | 0.01 | 8.03 | 5266.97 | 4969.20 | 19699.94 | 7750.11 |
| ILF2 | 0.01 | 1.44 | 13618.75 | 3364.73 | 19160.67 | 2735.72 |
| PTHLH | 0.01 | 6.69 | 6441.70 | 7953.95 | 19633.73 | 9861.15 |
| TRIB3 | 0.01 | 4.75 | 2091.17 | 2214.14 | 7387.63 | 5363.56 |
| MSI1 | 0.01 | 0.13 | 2616.70 | 1663.41 | 421.20 | 475.86 |
| IGFBP1 | 0.01 | 6.59 | 931.63 | 2215.31 | 3952.64 | 4619.23 |
| TMED9 | 0.01 | 1.30 | 11224.71 | 2442.54 | 14282.52 | 1309.85 |
| IL6 | 0.01 | 12.63 | 1869.99 | 2796.27 | 11071.49 | 7797.10 |
| CD36 | 0.01 | 0.45 | 13308.98 | 4037.75 | 6142.54 | 3025.02 |
| CDCP1 | 0.01 | 3.13 | 2578.14 | 1793.62 | 6624.40 | 2654.82 |
| B3GNT4 | 0.01 | 4.00 | 2393.20 | 2418.73 | 6054.66 | 3356.73 |
| G0S2 | 0.01 | 1.97 | 11673.35 | 5799.14 | 21565.14 | 7144.86 |

TABLE 3-continued

List of genes significantly differentially expressed between Prognosis subtypes 1 and 2.

| Gene | q. value | R. fold | Prognosis Subtype 1 Mean | Prognosis Subtype 1 SD | Prognosis Subtype 2 Mean | Prognosis Subtype 2 SD |
|---|---|---|---|---|---|---|
| TMCC3 | 0.01 | 0.44 | 274.45 | 318.11 | 78.09 | 9.91 |
| RARRES1 | 0.01 | 4.40 | 877.72 | 958.54 | 3050.94 | 2010.85 |
| PPP1R13B | 0.01 | 0.67 | 42295.88 | 7515.15 | 28350.28 | 5818.83 |
| LAMB3 | 0.01 | 5.19 | 1295.49 | 2012.96 | 4883.82 | 3909.33 |
| UBE2C | 0.01 | 2.85 | 1059.59 | 765.06 | 2522.13 | 1160.76 |
| RPL26L1 | 0.01 | 1.63 | 7649.03 | 2706.42 | 12071.41 | 2848.66 |
| SLC6A18 | 0.01 | 0.15 | 4033.38 | 6391.15 | 100.80 | 18.15 |
| HSD3B7 | 0.01 | 2.07 | 11014.58 | 6432.93 | 20571.02 | 7174.79 |
| SDPR | 0.01 | 0.22 | 1522.06 | 940.14 | 341.22 | 314.94 |
| ABCA12 | 0.01 | 5.20 | 480.44 | 415.90 | 2301.93 | 1504.30 |
| RARB | 0.01 | 0.38 | 2687.22 | 1102.62 | 1032.38 | 490.48 |
| GXYLT2 | 0.01 | 4.01 | 5156.94 | 4453.50 | 12491.42 | 4449.21 |
| EMCN | 0.01 | 0.14 | 7130.05 | 2572.85 | 1838.98 | 2335.68 |
| F2RL3 | 0.02 | 0.15 | 8055.35 | 5449.34 | 1685.99 | 2041.84 |
| ATP1B2 | 0.02 | 0.42 | 344.71 | 386.24 | 93.67 | 24.18 |
| PNPLA7 | 0.02 | 0.51 | 22112.68 | 4675.99 | 11732.24 | 4373.74 |
| SNORD78 | 0.02 | 1.72 | 6037.43 | 2431.38 | 9792.73 | 2374.50 |
| SLC6A19 | 0.02 | 0.20 | 1804.62 | 2186.33 | 150.45 | 105.00 |
| TIMELESS | 0.02 | 1.43 | 12956.99 | 3295.02 | 18022.91 | 2939.25 |
| GPRC5A | 0.02 | 4.63 | 4826.77 | 4537.78 | 12772.09 | 5006.02 |
| GRAMD1C | 0.02 | 0.35 | 370.07 | 390.16 | 90.48 | 47.34 |
| SRPX2 | 0.02 | 3.16 | 4013.34 | 3254.21 | 11279.39 | 6145.79 |
| TSTA3 | 0.02 | 2.64 | 3982.77 | 2454.89 | 8440.76 | 3228.31 |
| NUDT1 | 0.02 | 2.14 | 1552.81 | 875.10 | 3179.63 | 1321.63 |
| SHISA4 | 0.02 | 1.77 | 967.83 | 569.27 | 1544.70 | 398.83 |
| HSPC159 | 0.02 | 0.58 | 4829.10 | 1467.58 | 2805.99 | 934.44 |
| ADAM12 | 0.02 | 3.08 | 510.35 | 365.30 | 1409.79 | 605.81 |
| NOMO1 | 0.02 | 1.41 | 6920.06 | 1924.52 | 9613.80 | 1698.10 |
| TIPRL | 0.02 | 1.71 | 990.44 | 358.25 | 1653.15 | 488.74 |
| MRPS12 | 0.02 | 1.21 | 7714.22 | 802.63 | 9329.89 | 973.51 |
| MMP9 | 0.02 | 5.69 | 4988.74 | 4208.08 | 21201.30 | 15556.89 |
| HIST2H3C | 0.02 | 5.02 | 2303.06 | 2130.49 | 6786.64 | 4112.68 |
| RNF128 | 0.02 | 1.80 | 3769.33 | 1199.91 | 6758.63 | 2503.35 |
| LGSN | 0.02 | 0.28 | 572.34 | 602.79 | 109.70 | 99.75 |
| SLC9A3 | 0.02 | 0.17 | 3341.76 | 4618.18 | 349.19 | 416.19 |
| SOX8 | 0.02 | 0.12 | 4564.53 | 3560.46 | 929.41 | 1464.94 |
| AUTS2 | 0.02 | 0.57 | 19373.23 | 3306.57 | 11543.49 | 4626.93 |
| SLC39A1 | 0.02 | 1.24 | 15305.51 | 2179.30 | 18910.64 | 2179.79 |
| MIOX | 0.02 | 0.08 | 13111.28 | 7515.13 | 1802.21 | 1971.93 |
| RGS5 | 0.02 | 0.66 | 40485.22 | 5700.72 | 27324.05 | 6703.61 |
| PECAM1 | 0.02 | 0.62 | 18350.76 | 3858.62 | 11604.99 | 3634.17 |
| TRPM8 | 0.02 | 5.74 | 318.32 | 378.30 | 1697.47 | 1305.48 |
| GFPT2 | 0.02 | 13.91 | 391.18 | 720.30 | 4088.86 | 4168.47 |
| RANBP1 | 0.02 | 1.28 | 14423.19 | 2714.14 | 18210.15 | 2250.26 |
| C3orf71 | 0.02 | 0.42 | 384.37 | 604.97 | 74.61 | 11.05 |
| RHBDL2 | 0.02 | 2.29 | 506.95 | 559.64 | 810.42 | 298.25 |
| KCNE4 | 0.02 | 0.18 | 1221.87 | 1424.44 | 185.22 | 321.98 |
| C1R | 0.02 | 1.92 | 14156.01 | 7227.32 | 23310.54 | 5139.30 |
| PLOD2 | 0.02 | 1.26 | 24600.38 | 4623.15 | 30622.17 | 3447.21 |
| IVNS1ABP | 0.02 | 0.77 | 16167.92 | 2196.01 | 12503.06 | 2084.96 |
| SND1 | 0.02 | 1.39 | 7357.16 | 2047.46 | 9949.13 | 1553.75 |
| HIST2H3A | 0.02 | 2.44 | 3017.32 | 1640.84 | 6997.48 | 3282.49 |
| SPAG4 | 0.02 | 4.19 | 944.27 | 905.11 | 2703.90 | 1724.03 |
| PTTG1 | 0.03 | 2.55 | 3413.64 | 2018.54 | 6923.91 | 2785.22 |
| PHF1 | 0.03 | 0.71 | 15466.02 | 2806.57 | 11095.66 | 2229.15 |
| C5orf46 | 0.03 | 5.84 | 6436.88 | 7059.01 | 16967.96 | 9955.13 |
| SLC22A12 | 0.03 | 0.15 | 5367.45 | 4545.15 | 944.03 | 1032.47 |
| AGTR1 | 0.03 | 0.21 | 3255.00 | 3016.64 | 628.76 | 585.23 |
| PSMD14 | 0.03 | 1.39 | 7875.00 | 2200.16 | 10668.21 | 1715.25 |
| CXCL5 | 0.03 | 9.19 | 195.44 | 372.29 | 2151.50 | 1844.54 |
| IDH1 | 0.03 | 1.75 | 2973.17 | 955.92 | 5258.68 | 1988.51 |
| PLAT | 0.03 | 0.55 | 11980.85 | 3772.90 | 6618.52 | 2408.05 |
| NEFL | 0.03 | 2.69 | 16495.66 | 13376.70 | 32780.54 | 12463.63 |
| CPM | 0.03 | 0.55 | 4182.38 | 1303.46 | 2327.10 | 846.03 |
| PADI4 | 0.03 | 0.29 | 1110.93 | 1312.93 | 171.64 | 106.03 |
| KDR | 0.03 | 0.36 | 7657.95 | 2956.14 | 3128.36 | 1821.88 |
| IL1R2 | 0.03 | 3.09 | 1176.97 | 1243.79 | 3178.45 | 2300.68 |
| HOTAIR | 0.03 | 0.27 | 861.92 | 922.39 | 146.96 | 143.07 |
| G6PC | 0.03 | 0.09 | 6369.61 | 5723.08 | 1047.48 | 1599.24 |
| MAGED1 | 0.03 | 1.39 | 10911.15 | 2612.86 | 14978.58 | 2875.12 |
| GMPPA | 0.03 | 1.56 | 3386.76 | 1102.11 | 5152.45 | 1375.77 |
| CDR2 | 0.03 | 1.95 | 813.52 | 533.19 | 1374.27 | 507.74 |
| TFIP11 | 0.03 | 1.41 | 7714.60 | 1503.71 | 10949.21 | 2743.95 |

TABLE 3-continued

List of genes significantly differentially expressed between Prognosis subtypes 1 and 2.

| Gene | q. value | R. fold | Prognosis Subtype 1 Mean | Prognosis Subtype 1 SD | Prognosis Subtype 2 Mean | Prognosis Subtype 2 SD |
|---|---|---|---|---|---|---|
| STEAP3 | 0.03 | 1.83 | 3492.48 | 797.29 | 6733.09 | 2748.95 |
| TMED3 | 0.03 | 1.30 | 24669.33 | 3174.73 | 32213.75 | 5136.95 |
| WT1 | 0.03 | 6.95 | 718.66 | 1168.99 | 2785.68 | 2041.81 |
| KLHL4 | 0.03 | 8.99 | 293.22 | 509.57 | 2244.72 | 1688.17 |
| DSN1 | 0.03 | 1.52 | 8991.83 | 2590.53 | 13481.01 | 3544.08 |
| MOGS | 0.03 | 1.49 | 9123.15 | 3058.61 | 12947.63 | 2643.80 |
| PNKD | 0.03 | 1.79 | 5442.82 | 2108.12 | 9636.16 | 3638.06 |
| PSMG3 | 0.03 | 3.52 | 401.33 | 350.68 | 1139.42 | 563.20 |
| CYP1B1 | 0.03 | 2.97 | 3589.24 | 2886.74 | 7466.17 | 3150.56 |
| C1orf117 | 0.03 | 5.31 | 1033.97 | 1467.58 | 2811.54 | 1911.20 |
| B3GAT3 | 0.03 | 2.74 | 2710.42 | 1694.24 | 5293.41 | 2097.10 |
| TUBA1A | 0.03 | 1.36 | 23827.72 | 5695.64 | 31936.94 | 5864.45 |
| CD82 | 0.03 | 1.73 | 2995.34 | 987.65 | 5238.59 | 1954.52 |
| GOLSYN | 0.03 | 6.94 | 1107.34 | 1425.21 | 4308.70 | 3186.70 |
| PDGFRL | 0.03 | 3.46 | 3218.74 | 2619.40 | 8990.74 | 4508.20 |
| NEB | 0.03 | 5.37 | 768.54 | 1709.39 | 3361.68 | 3710.18 |
| TMEM45A | 0.03 | 2.54 | 3039.47 | 2519.30 | 5447.44 | 1844.59 |
| OBFC2B | 0.03 | 2.67 | 4391.14 | 2492.56 | 8814.26 | 3534.06 |
| LOC653604 | 0.03 | 2.52 | 6280.04 | 2741.96 | 13158.67 | 4437.94 |
| SERPINA5 | 0.04 | 2.58 | 331.45 | 301.81 | 797.15 | 547.28 |
| SLC19A3 | 0.04 | 1.77 | 15002.93 | 7349.70 | 24208.80 | 6971.49 |
| SERPINA3 | 0.04 | 15.12 | 600.16 | 1313.92 | 7220.24 | 7349.07 |
| ANAPC11 | 0.04 | 1.57 | 3566.78 | 1141.81 | 5548.05 | 1850.44 |
| RCN1 | 0.04 | 1.19 | 15840.27 | 2089.52 | 18846.90 | 1946.14 |
| TNIP2 | 0.04 | 1.86 | 2319.03 | 1180.42 | 4177.59 | 1921.20 |
| SNORD83A | 0.04 | 1.29 | 26374.70 | 4606.54 | 33810.72 | 5363.56 |
| KCNG1 | 0.04 | 3.51 | 247.90 | 187.88 | 960.40 | 879.42 |
| USP1 | 0.04 | 2.30 | 720.81 | 443.87 | 1348.10 | 595.69 |
| TBX18 | 0.04 | 2.23 | 218.05 | 142.79 | 472.71 | 240.90 |
| SLITRK2 | 0.04 | 4.32 | 3694.49 | 3754.85 | 8343.69 | 6095.61 |
| KDELR2 | 0.04 | 1.32 | 11824.82 | 2520.56 | 15525.01 | 2816.41 |
| ARMET | 0.04 | 1.34 | 19602.19 | 4371.38 | 26039.10 | 5453.29 |
| POP7 | 0.04 | 1.46 | 14696.18 | 4082.27 | 21225.29 | 4591.96 |
| RASGEF1C | 0.04 | 3.32 | 420.55 | 289.63 | 1543.87 | 1180.95 |
| LGALS1 | 0.04 | 1.26 | 28437.27 | 4116.78 | 35722.06 | 5439.03 |
| MGC5139 | 0.04 | 2.42 | 2947.56 | 1963.00 | 5594.60 | 2648.39 |
| SPOCK1 | 0.04 | 3.22 | 4504.99 | 4992.34 | 11127.36 | 7300.38 |
| NUP62 | 0.04 | 1.17 | 17428.86 | 1801.70 | 20302.79 | 2002.33 |
| ARL4C | 0.04 | 2.09 | 549.72 | 300.12 | 1126.80 | 596.83 |
| LOC730347 | 0.04 | 2.17 | 2811.49 | 1765.40 | 4949.16 | 1691.70 |
| FABP6 | 0.04 | 3.31 | 9199.16 | 6736.40 | 23030.53 | 14403.94 |
| KIAA1244 | 0.04 | 2.87 | 747.48 | 588.06 | 1806.86 | 872.23 |
| CLEC16A | 0.04 | 1.25 | 16304.25 | 3061.72 | 20247.88 | 2565.45 |
| SLC2A1 | 0.04 | 1.28 | 13905.90 | 2717.29 | 17594.25 | 2386.18 |
| HK2 | 0.04 | 2.04 | 1144.94 | 660.80 | 2137.48 | 962.07 |
| PDIA6 | 0.04 | 1.33 | 10335.70 | 2265.40 | 13602.50 | 2462.30 |
| ANLN | 0.04 | 2.00 | 2042.31 | 1039.76 | 3547.06 | 1238.50 |
| LPAR2 | 0.04 | 1.73 | 1339.13 | 726.76 | 2025.40 | 586.99 |
| MDM2 | 0.04 | 1.36 | 7460.56 | 1639.34 | 10101.95 | 1903.06 |
| PPIB | 0.04 | 1.30 | 14737.26 | 3450.28 | 18853.32 | 2921.23 |
| NCAM1 | 0.04 | 6.25 | 1025.39 | 1072.53 | 7226.46 | 5917.43 |
| PRAME | 0.04 | 9.84 | 431.97 | 722.63 | 4797.21 | 5023.85 |
| ARPC1B | 0.04 | 1.26 | 16618.74 | 2912.39 | 20889.46 | 3187.11 |
| NUDT5 | 0.04 | 2.33 | 3148.63 | 1991.61 | 6246.28 | 2918.45 |
| C3 | 0.04 | 1.46 | 20173.35 | 7404.26 | 27838.40 | 5422.49 |
| SNORD88C | 0.04 | 1.31 | 12948.89 | 3757.04 | 16413.60 | 2424.29 |
| COL22A1 | 0.04 | 8.22 | 321.92 | 559.54 | 2753.71 | 3864.98 |
| PYGO2 | 0.04 | 2.06 | 2853.56 | 1614.03 | 4811.90 | 1602.52 |
| FN1 | 0.04 | 1.22 | 31291.54 | 4665.65 | 38000.05 | 4653.10 |
| PSMC4 | 0.04 | 1.46 | 4979.45 | 1680.57 | 6995.79 | 1551.24 |
| HM13 | 0.04 | 1.27 | 8337.88 | 1109.64 | 10683.99 | 2139.23 |
| BUD13 | 0.04 | 2.09 | 1315.15 | 752.01 | 2621.05 | 1657.03 |
| LRWD1 | 0.04 | 1.88 | 1960.54 | 1007.66 | 3072.47 | 933.63 |
| CXCL1 | 0.04 | 1.66 | 3105.68 | 1698.17 | 4489.29 | 1029.72 |
| QSOX1 | 0.04 | 1.71 | 2118.22 | 663.00 | 3767.46 | 1771.45 |
| SNORA71C | 0.04 | 1.47 | 9011.31 | 3219.43 | 12675.94 | 2903.71 |

TABLE 3-continued

List of genes significantly differentially
expressed between Prognosis subtypes 1 and 2.

| Gene | q. value | R. fold | Prognosis Subtype 1 Mean | Prognosis Subtype 1 SD | Prognosis Subtype 2 Mean | Prognosis Subtype 2 SD |
|---|---|---|---|---|---|---|
| POMT2 | 0.04 | 2.49 | 2862.90 | 2098.33 | 5999.21 | 3637.75 |
| CBX8 | 0.04 | 1.99 | 2970.56 | 1684.57 | 5320.43 | 2315.35 |
| FBF1 | 0.04 | 2.47 | 270.72 | 289.88 | 555.44 | 297.07 |
| GPATCH4 | 0.04 | 1.79 | 1642.15 | 956.83 | 2518.50 | 750.32 |
| F8A3 | 0.04 | 1.85 | 999.66 | 758.57 | 1507.96 | 435.39 |
| VSIG4 | 0.04 | 2.25 | 341.93 | 254.50 | 746.76 | 431.58 |
| GCNT3 | 0.04 | 7.66 | 1312.74 | 1687.81 | 5389.18 | 4069.88 |
| PRKDC | 0.04 | 1.28 | 10418.59 | 2036.98 | 13212.66 | 2059.89 |
| MED8 | 0.04 | 1.55 | 2065.10 | 734.24 | 3135.14 | 922.28 |
| LGALS3BP | 0.04 | 1.60 | 7812.87 | 3036.80 | 12232.48 | 3953.69 |
| C1orf35 | 0.04 | 2.59 | 1137.04 | 766.63 | 2533.97 | 1391.58 |
| C11orf48 | 0.04 | 1.43 | 5177.48 | 2207.45 | 7013.08 | 1430.97 |
| MIR210 | 0.04 | 3.02 | 2837.84 | 1931.78 | 5805.25 | 3066.74 |
| SLC7A5P1 | 0.04 | 1.96 | 6131.99 | 2648.39 | 10379.97 | 2987.96 |
| SPP1 | 0.04 | 1.20 | 40041.43 | 5945.15 | 47925.17 | 5558.27 |
| PSMB4 | 0.04 | 1.37 | 7695.26 | 1949.18 | 10370.90 | 2144.71 |
| RPTOR | 0.04 | 2.46 | 1988.63 | 1173.89 | 3981.19 | 2126.65 |
| LOC100128731 | 0.04 | 1.19 | 28519.44 | 3852.65 | 33884.81 | 3774.57 |
| SEMA4F | 0.04 | 3.31 | 1045.97 | 930.08 | 2906.89 | 2207.10 |
| PATE2 | 0.04 | 1.60 | 278.78 | 118.54 | 437.78 | 141.35 |
| C12orf57 | 0.04 | 1.80 | 3088.65 | 1777.46 | 4837.80 | 1412.47 |
| TAGLN2 | 0.04 | 1.21 | 23283.51 | 3205.06 | 28266.89 | 3700.43 |
| PSMA5 | 0.04 | 1.40 | 15420.83 | 4581.14 | 21223.75 | 4486.60 |
| SNORD37 | 0.04 | 1.32 | 15577.80 | 2364.61 | 20698.82 | 4146.51 |
| PSMB3 | 0.04 | 1.31 | 17435.08 | 3601.29 | 22745.00 | 4145.14 |
| CCDC97 | 0.04 | 1.38 | 7777.20 | 2637.50 | 10209.00 | 1726.19 |
| ARPC1A | 0.04 | 1.30 | 15340.75 | 3646.75 | 19694.30 | 3457.62 |
| LONP1 | 0.04 | 1.35 | 14402.92 | 3878.06 | 19191.42 | 3808.25 |
| CSNK1D | 0.05 | 1.17 | 19638.21 | 3069.24 | 22891.03 | 2213.97 |
| CDCA3 | 0.05 | 2.46 | 4403.47 | 3203.44 | 9312.46 | 4525.62 |
| SFT2D1 | 0.05 | 2.13 | 3094.38 | 2231.55 | 4803.86 | 1427.04 |
| PDPN | 0.05 | 3.04 | 908.04 | 760.73 | 2600.69 | 2195.71 |
| NME2 | 0.05 | 1.29 | 4250.92 | 862.28 | 5448.03 | 946.46 |
| NUF2 | 0.05 | 2.47 | 593.66 | 360.37 | 1405.52 | 759.75 |
| TFAP2A | 0.05 | 2.56 | 198.66 | 189.96 | 479.09 | 326.65 |
| C1S | 0.05 | 1.78 | 10576.96 | 5285.45 | 17097.44 | 4818.86 |
| KIAA1715 | 0.05 | 1.76 | 3323.82 | 1406.42 | 5550.09 | 2102.36 |
| C17orf58 | 0.05 | 1.89 | 2285.68 | 893.56 | 3916.49 | 1415.70 |
| DHCR24 | 0.05 | 2.23 | 639.67 | 374.97 | 1344.86 | 693.28 |
| TREM1 | 0.05 | 2.47 | 282.49 | 161.14 | 756.12 | 512.59 |
| C9orf140 | 0.05 | 2.29 | 1120.27 | 817.81 | 2130.00 | 994.48 |
| IL10RB | 0.05 | 1.55 | 1919.54 | 895.28 | 2750.80 | 697.57 |
| SCARNA20 | 0.05 | 1.55 | 16418.28 | 5117.96 | 25271.34 | 7798.24 |
| SEC23B | 0.05 | 1.20 | 10747.90 | 2345.62 | 12624.34 | 1010.84 |
| HIST2H4B | 0.05 | 1.20 | 8614.78 | 1475.84 | 10265.09 | 1148.24 |

SD: standard deviation

Figure 3:
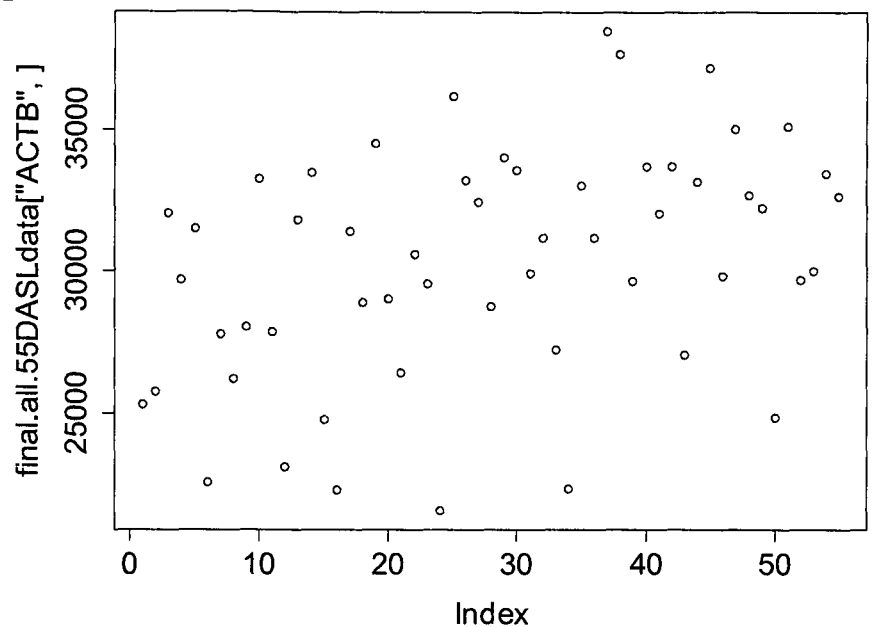
FIG. 3 shows dotplots for expression of four genes in 55 samples.
Figure 3:
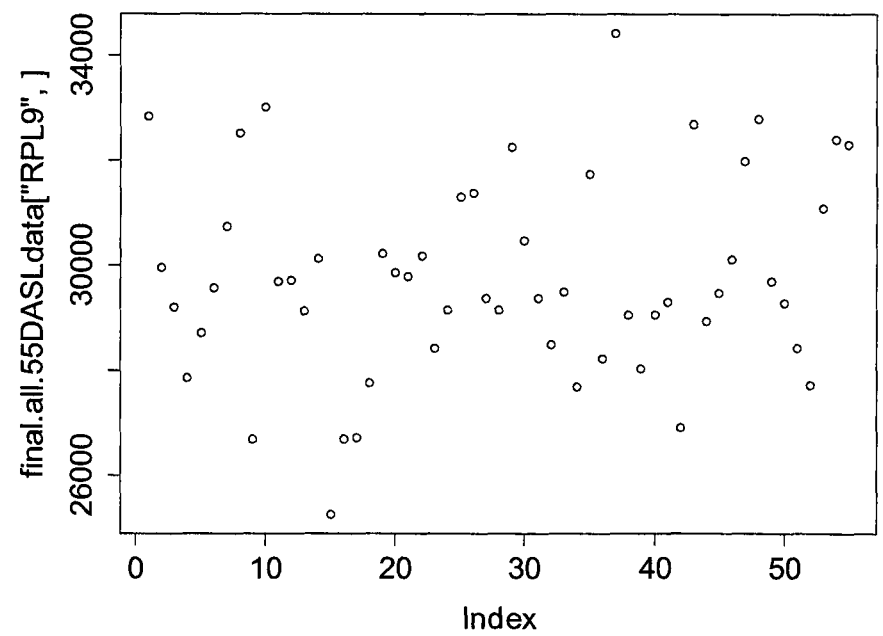
Figure 3:
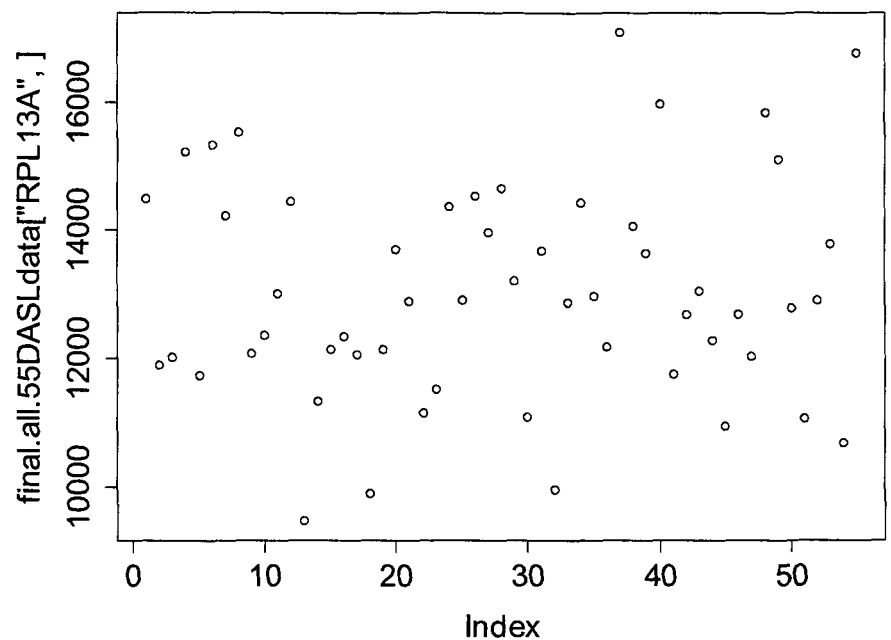
Figure 3:
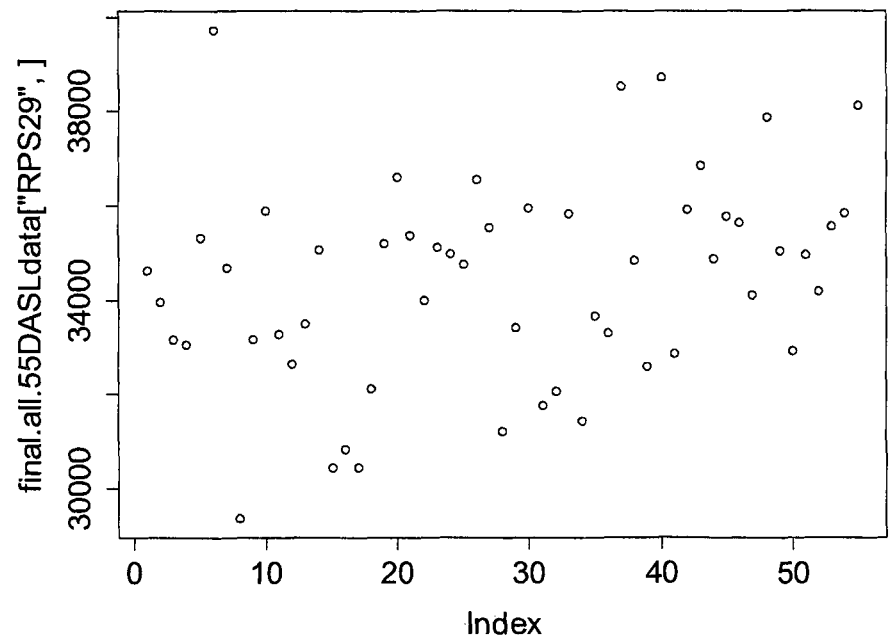

As the aim was to identify prognostic subtypes- and implement, an expression-based method to classify ccRCCs into these prognostic subtypes, qPCR assays were designed for a set of 37 genes that were previously identified as prognostic genes on DASL platform. Expression levels measured by DASL method was reproduced by qPCR for these 37 genes in 6 randomly selected tumour samples that were also assessed by DASL assay. The list of selected genes and the primer sequences used to produce amplicons amenable to PCR amplification from FFPE RNA are described in Table 4. Separately, four genes (β-actin, RPL9, RPL13A, RPS29) whose expression was the least variable (lowest coefficients of variance) among the 55 ccRCCs were also identified to serve as normalization genes for qPCR (FIG. 3). Based on the initial success of translation of expression quantification on the qPCR platform, 18 genes were selected which were, measurable by qPCR on FFPE RNA, and closely compatible in their measured expression on qPCR and DASL platforms.

TABLE 4

List of prognostic and normalization genes and primers used to measure their expression levels using qPCR.

| Gene | Forward Primer | Reverse Primer |
|---|---|---|
| AGTR1_v1 | GTC GGC ACC AGG TGT ATT T (SEQ ID NO. 1) | CCA TCT TCA GTA GAA GAG TTG (SEQ ID NO. 2) |
| AGTR1_v3 | GCT CAG AGG AGG TGT ATT TGA (SEQ ID NO. 3) | CCA TCT TCA GTA GAA GAG TTG (SEQ ID NO. 4) |
| CTHRC1 | GTG GTG GAC CTG TAT AAT GGA AT (SEQ ID NO. 5) | GAA TGC CAT TGG CCC CAG (SEQ ID NO. 6) |
| CXCL5 | CGC AAG GAG TTC ATC CCA (SEQ ID NO. 7) | CAG GGA GGC TAC CAC TT (SEQ ID NO. 8) |

TABLE 4-continued

List of prognostic and normalization genes and primers used to measure their expression levels using qPCR.

| Gene | Forward Primer | Reverse Primer |
|---|---|---|
| EFNA5 | CAG CAG ATG ACA CCG TAC A (SEQ ID NO. 9) | CAA AAG GCG GCT GGG TAT C (SEQ ID NO. 10) |
| EMCN | GAT CAA CCT CAG TCT GAT AAA GAG (SEQ ID NO. 11) | GTG CAG AGT GCT CAC CAG AC (SEQ ID NO. 12) |
| F2RL3 | AGG TGG TGA TGA CAG CAC (SEQ ID NO. 13) | CCA GGG TGT CAC TGT CAT T (SEQ ID NO. 14) |
| G6PC | CTG TCA GGC ATT GCT GTT G (SEQ ID NO. 15) | CTT GAG GCT GGC ATT ATA GAT (SEQ ID NO. 16) |
| GFPT2 | GAG GAT ATG ACG TTG ACT TCC (SEQ ID NO. 17) | CAT TCC ACA GTT ACA GAC TTG GC (SEQ ID NO. 18) |
| HIST2H3C | CAG AAG TCC ACG GAG CT (SEQ ID NO. 19) | CAG GTC CGT CTT AAA GTC CT (SEQ ID NO. 20) |
| IGFBP1 | CAG ACA GTG TGA GAC ATC CA (SEQ ID NO. 21) | CCT CTT CCC ATT CCA AGG GT (SEQ ID NO. 22) |
| IL6 | GAT TCA ATG AGG AGA CTT GCC (SEQ ID NO. 23) | CTC TCA AAT CTG TTC TGG AGG T (SEQ ID NO. 24) |
| KDELR3_v1 | CTT GTA TGT GAC CAA AGT CCT (SEQ ID NO. 25) | CGT AGA CTG TCT CTG AAG GT (SEQ ID NO. 26) |
| KDELR3_v2 | GCT GGA GAT CCT CTG GAC TT (SEQ ID NO. 27) | GAT CAG CAA GAC TGG AGA G (SEQ ID NO. 28) |
| KDR | CCA GAT GAC AAC CAG ACG GA (SEQ ID NO. 29) | CTG GGC ACC ATT CCA CCA A (SEQ ID NO. 30) |
| KLHL4 | CTG TGT GGA ACG GTA TGA TC (SEQ ID NO. 31) | GAG GAA CAC TCA GAG GTG CCA (SEQ ID NO. 32) |
| LAMB3 | CAG AGG CAG AGG AGC TGT T (SEQ ID NO. 33) | CCA ACT CCA TGT CTT TCA TCC (SEQ ID NO. 34) |
| MIOX | GTG CGG GAG TTC AAC AAG TTC (SEQ ID NO. 35) | GTC AAT GAG CCC CTG GT (SEQ ID NO. 36) |
| MMP9 | CAG TAC CGA GAG AAA GCC TA (SEQ ID NO. 37) | CCA CCT GGT TCA ACT CAC TC (SEQ ID NO. 38) |
| MOCOS | GGT GAA TGA GGC ACA GTA TC (SEQ ID NO. 39) | CTT TCC ATT CTC ATC ACT GGT G (SEQ ID NO. 40) |
| MSI1 | TCG AGG GAC AGG CTC TCA (SEQ ID NO. 41) | TGG GAG TCG AAC CTG GA (SEQ ID NO. 42) |
| NUDT5 | CCA GGG GAT GGA GAG TTT G (SEQ ID NO. 43) | GTT CTT CAG CTA CCA GAG CA (SEQ ID NO. 44) |
| PLG | ATG GCT GAA AAC AGG AAG TC (SEQ ID NO. 45) | CCT CCA TAA TCA TTA GGA TGA GAG (SEQ ID NO. 46) |
| PRAME | GGA TCA GTT GCT CAG GCA C (SEQ ID NO. 47) | CAT CAC ATC CCC TTC CGA A (SEQ ID NO. 48) |
| PTHLH | CGC CTC AAA AGA GCT GTG (SEQ ID NO. 49) | GTG AAG GAA GAA TCG TCG CC (SEQ ID NO. 50) |
| RARRES1 | GGC AGT GGA AAA CTA ATG ATG A (SEQ ID NO. 51) | CAG GGA ATT ATT TCC TGT GTT G (SEQ ID NO. 52) |
| RGS7BP | TCA AGA TGA CAG CAG CCT TCT (SEQ ID NO. 53) | GAA CCT TCT CTT CCG TCT TC (SEQ ID NO. 54) |
| SDPR | GCT CAT CTT CCA GGA GGA AA (SEQ ID NO. 55) | CTC CTC CTT CCC TTC CAC (SEQ ID NO. 56) |
| SERPINA3 | GTC TCC CAG GTG GTC CAT AA (SEQ ID NO. 57) | GGA GGG TGA TTT TGA CTG C (SEQ ID NO. 58) |
| SLC6A19 | GAC CCT GGC TAC GAG GAA T (SEQ ID NO. 59) | CCA GTT CGG GTA GGA GAT C (SEQ ID NO. 60) |
| SLC9A3 | CCA TCA GGA GAA AAG ACT GGA (SEQ ID NO. 61) | CTA GCC AGG AAC TCG ATC C (SEQ ID NO. 62) |
| TK1 | AGA AGG AGG TCG AGG TGA TT (SEQ ID NO. 63) | GCC TGA GGC TTC TT GAA G (SEQ ID NO. 64) |
| TRPM8 | CAG AGG AAA TGA GGC ATC G (SEQ ID NO. 65) | CCT TGA GAT CAT TAA GCT TTG TAT CC (SEQ ID NO. 66) |
| TSPAN7 | GGA ATC GCA TTC TCC CAG T (SEQ ID NO. 67) | CGT CAT TCT TGA AAG ACT TCT CC (SEQ ID NO. 68) |
| TUBB3 | CAT CTT TGG TCA GAG TGG GG (SEQ ID NO. 69) | CAC ATC CAG GAC CGA ATC C (SEQ ID NO. 70) |
| VIPR1 | GTA CAC TAC ATC ATG TTC GCC (SEQ ID NO. 71) | CCA CAA AAC CCT GGA AAG AC (SEQ ID NO. 72) |
| WT1 | GGA AGC ACA CTG GTG AGA A (SEQ ID NO. 73) | CCT TCG TTC ACA GTC CTT GA (SEQ ID NO. 74) |
| ACTB* | CAA GAT CAT TGC TCC TCC TG (SEQ ID NO. 75) | CCA CAT CTG CTG GAA GGT G (SEQ ID NO. 76) |
| RPL13A* | CAC TTG GGG ACA GCA TGA G (SEQ ID NO. 77) | GTA ACC CTT GGC TTG TGC AT (SEQ ID NO. 78) |
| RPL9* | CGG ATG AGA CCA GGT GTT G (SEQ ID NO. 79) | CAA GCT CAA TGT CAT TTC CTT C (SEQ ID NO. 80) |

TABLE 4-continued

List of prognostic and normalization genes and primers used to measure their expression levels using qPCR.

| Gene | Forward Primer | Reverse Primer |
|---|---|---|
| RPS29* | GCT CTT GTC GTG TCT GTT C (SEQ ID NO: 81) | CGT ACT GAC GGA AAC ACT G (SEQ ID NO. 82) |

*Normalization genes v1 and v2 refer to different transcript variants of the same gene for which unique primers were designed.

Figure 4:
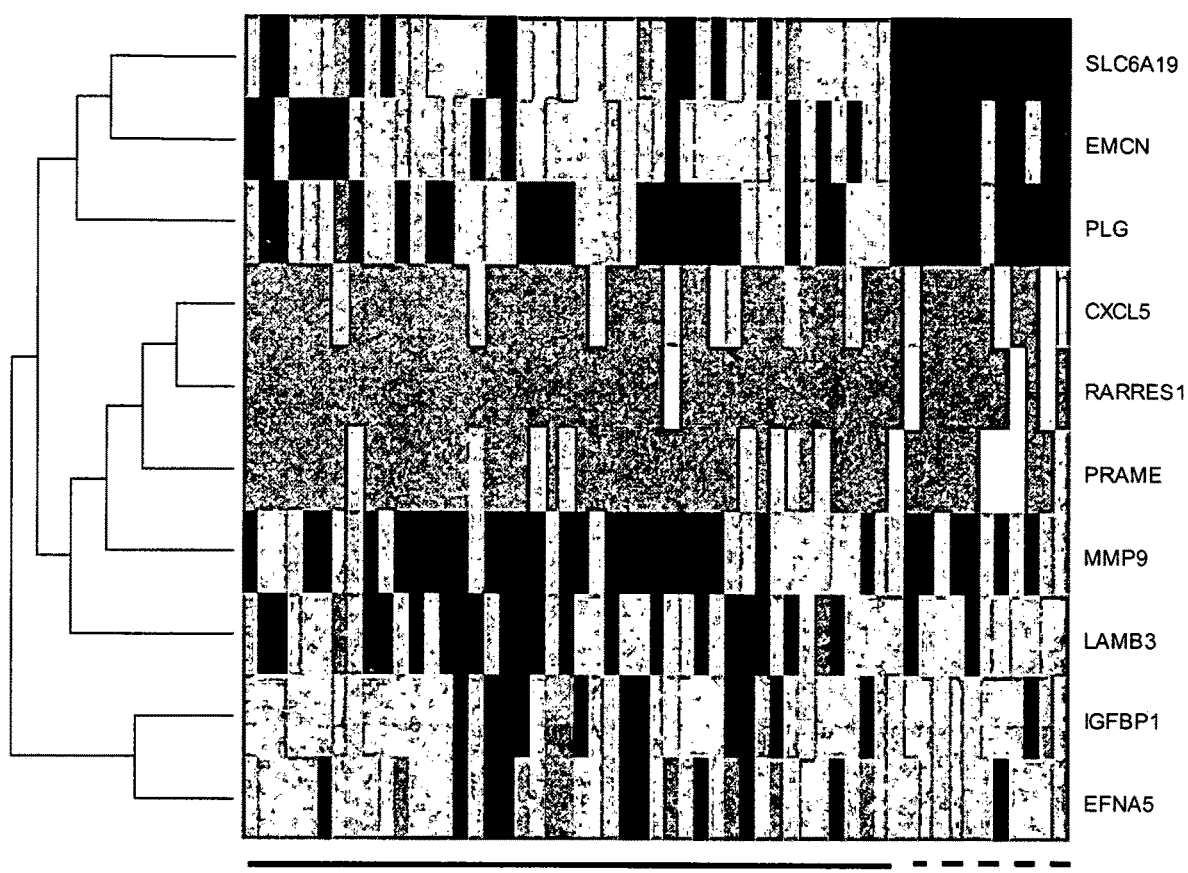
FIG. 4. Heatmap of expression of 10 prognostic genes.

These 18 genes were quantified in all 55 ccRCCs by qPCR and the correlation of expressions between qPCR and DASL platforms was calculated to determine those genes with the best performance on the qPCR platform, thus embodying the ideal nature of a prognostic gene determined on a distinct platform. 10 genes which were the most significantly correlated (Pearson's correlation p<0.05) in expression between the two platforms were selected (Table 5). Ten genes with the highest correlation were selected as the final prognostic gene set. These included CXCL5, EFNA5, EMCN, IGFBP1, LAMB3, MMP9, PLG, PRAME, RARRES1 and SLC6A19. Univariate logistic correlation analysis for qPCR gene expression with DASL prognosis subtype classification showed that their direction of association was as expected and significant for most prognostic genes (Table 6 and FIG. 4).

TABLE 5

Correlation of expression levels determined by DASL assay and qPCR for 18 prognostic genes.

| Gene | Correlation coefficient | t | p-value |
|---|---|---|---|
| MMP9 | 0.789638 | 9.3691 | 7.81E-13 |
| PRAME | 0.708578 | 7.3105 | 1.43E-09 |
| CXCL5 | 0.581672 | 5.2059 | 3.2E-06 |
| LAMB3 | 0.57174 | 5.0733 | 5.13E-06 |
| RARRES1 | 0.518783 | 4.4178 | 4.96E-05 |
| PLG | 0.472899 | 3.9073 | 0.000267 |
| SLC6A19 | 0.467393 | 3.849 | 0.000321 |
| EFNA5 | 0.373134 | 2.9279 | 0.005019 |
| IGFBP1 | 0.322731 | 2.4823 | 0.01625 |
| EMCN | 0.267176 | 2.0184 | 0.04862 |
| HIST2H3C | 0.205662 | 1.5299 | 0.132 |
| GFPT2 | 0.169278 | 1.2504 | 0.2166 |
| G6PC | 0.104169 | 0.7625 | 0.4491 |
| TSPAN7 | 0.097224 | 0.7112 | 0.4801 |
| TK1 | 0.062664 | 0.4571 | 0.6495 |
| MOCOS | 0.062524 | 0.4561 | 0.6502 |
| KDELR3 | 0.06103 | 0.4451 | 0.658 |
| SDPR | -0.08401 | -0.6138 | 0.542 |

TABLE 6

Univariate logistic regression analysis for 10 prognostic genes and prognostic subtype assignment.

| Gene | Estimate | Std. Error | t value | Pr (>|t|) |
|---|---|---|---|---|
| SLC6A19 | -0.04188 | 0.00783 | -5.348 | 1.93E-06 |
| EMCN | -0.03883 | 0.009622 | -4.036 | 0.000176 |
| PLG | -0.02696 | 0.008596 | -3.137 | 0.00279 |
| PRAME | 0.04576 | 0.01543 | 2.966 | 0.00451 |
| RARRES1 | 0.05143 | 0.01989 | 2.586 | 0.0125 |
| LAMB3 | 0.02465 | 0.01042 | 2.366 | 0.0217 |
| CXCL5 | 0.04105 | 0.02068 | 1.985 | 0.0524 |
| EFNA5 | 0.0215 | 0.01154 | 1.863 | 0.068 |

TABLE 6-continued

Univariate logistic regression analysis for 10 prognostic genes and prognostic subtype assignment.

| Gene | Estimate | Std. Error | t value | Pr (>|t|) |
|---|---|---|---|---|
| IGFBP1 | 0.01722 | 0.01087 | 1.585 | 0.119 |
| MMP9 | 0.01845 | 0.01234 | 1.496 | 0.141 |

The requirement to develop a prognostic model based on qPCR assays for a limited gene set that can reproduce classification patterns achieved by the DASL expression analysis, dictated that the ten selected prognostic genes are able to reconstruct the sample, distribution of good and poor prognosis subtypes originally produced. Therefore, these ten genes were used for developing a prognostic algorithm using a multivariate logistic correlation analysis for dichotomized outcome corresponding to prognostic subtype assignment (good or poor prognosis) determined by DASL expression analysis. The algorithm based on normalized and scaled Ct values for each gene is summarized in Table 7 with coefficients. The scoring formula is described as the linear combination below:

$$-0.00534 \times CXCL5 - 0.0111 \times LAMB3 + 0.001578 \times MMP9 - 0.02952 \times PRAME - 0.01001 \times RARRES1 + 0.012535 \times PLG + 0.021832 \times SLC6A19 - 0.01494 \times EFNA5 + 0.014457 \times IGFBP1 + 0.020579 \times EMCN$$

TABLE 7

Summary of algorithm coefficients values for qPCR expression of 10 genes derived from the 55 ccRCC screening cohort.

| Gene Coefficients | Value |
|---|---|
| CXCL5 | -0.00534 |
| LAMB3 | -0.0111 |
| MMP9 | 0.001578 |
| PRAME | -0.02952 |
| RARRES1 | -0.01001 |
| PLG | 0.012535 |
| SLC6A19 | 0.021832 |
| EFNA5 | -0.01494 |
| IGFBP1 | 0.014457 |
| EMCN | 0.020579 |
| Intercept | 0.578108 |

The scoring algorithm was used to derive a prognostic score for each of the 55 ccRCCs in the screening cohort and a cut-off value for assignment to good or poor subtypes was selected such that misclassification of samples was minimized.

Figure 5:
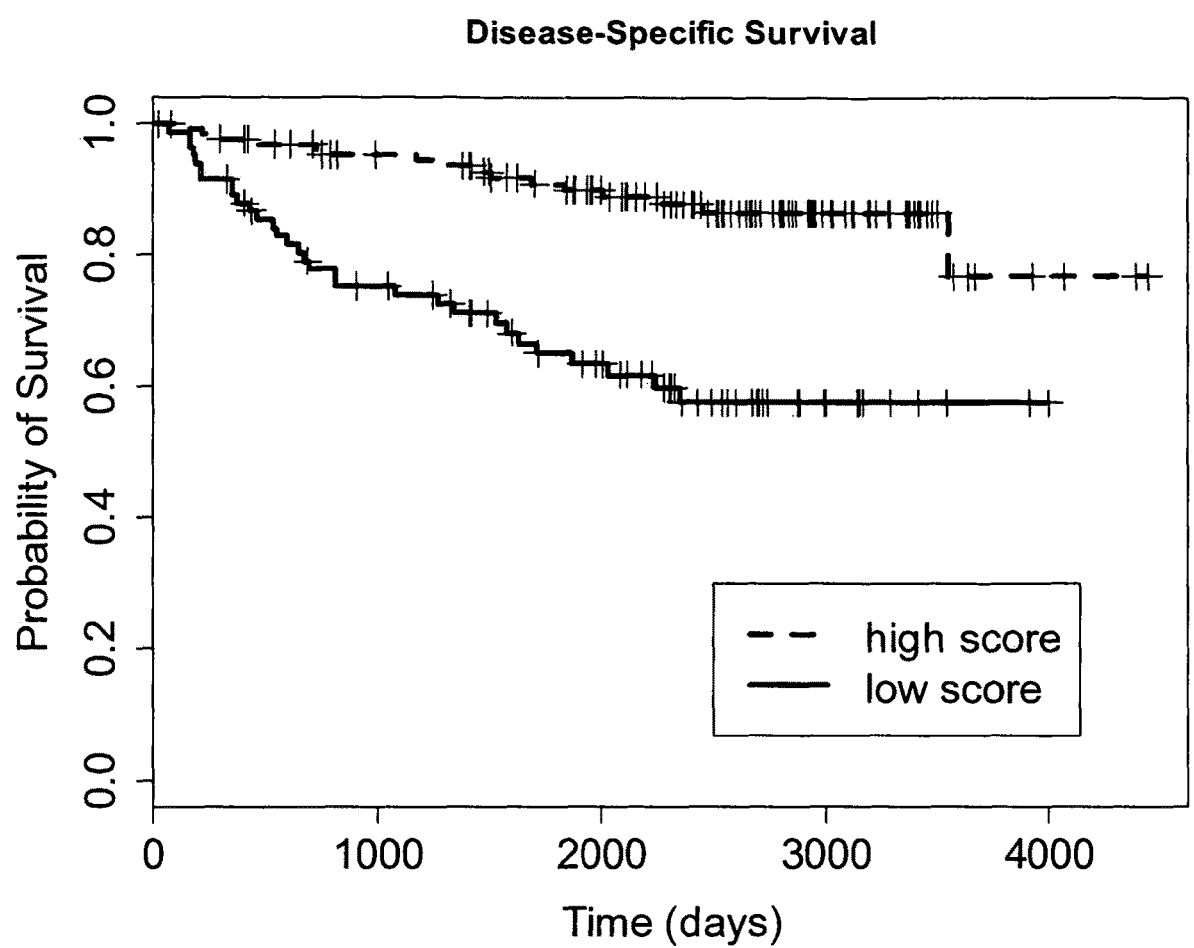
FIG. 5. Prognostic utility of ten-gene scoring algorithm for ccRCCs.

To validate the performance of the ten-gene prognostic algorithm in a separate confirmation cohort of 214 ccRCCs, prognostic scores were calculated based on the qPCR expression values of these ten genes with weighted coefficients determined by multivariate logistic correlation. QPCR expression data was processed in the same manner as it was for the 55 ccRCC screening cohort and Ct values (only those less than 36 considered) were normalized to housekeeping genes and scaled to lie on a positive scale by the addition of a positive constant (14.72). Based on the cutoff determined from the screening cohort, samples were assigned to high- and low-scoring categories corresponding to good and poor prognosis subtypes respectively. Kaplan-Meier analysis showed a significant difference in disease-specific survival between high- and low-scoring groups (FIG. 5) (p=2.49e-06 by log rank test). Multivariate analysis by Cox proportional hazards modeling demonstrated that the prognostic score as a continuous variable remained significant after adjusting singly for standard clinicopathologic parameters, including age, tumour stage and grade (Table 8).

TABLE 8

Multivariate analysis of 10-gene prediction score and clinicopathologic features

| Adjusted variable | Adjusted hazard ratio of predictor | 95% confidence intervals | p-value LR test |
|---|---|---|---|
| Unadjusted | 9.578 | 3.61-25.4 | 0.000003527 |
| Age | 7.8576 | 2.89-21.3 | 7.138E−07 |
| Stage Group | 5.857 | 1.7-20.0 | 0 |
| Grade | 6.181 | 2.1-17.9 | 2.513E−07 |

For a subset of patients of 38 patients from the patient cohort that received TKI treatment in first-, second- or third-line setting, stratification was done based on the prognostic score into high- and low-scoring groups. For two patients, no evaluable clinical response was available. There was a statistically significant difference between number of clinical responders in the two prognostic groups (Table 9) (response rates 51% vs. 100%, p=0.01361 by Fisher's exact test). Further, univariate logistic regression analysis with dichotomized objective response and prognostic score suggested that the score tends to significance (p=0.0535).

TABLE 9

Clinical response count data for 36 TKI-receiving patients classified into prognosis categories based on 10-gene prognostic score.

| | Prognosis Subtype 1 | Prognosis Subtype 2 |
|---|---|---|
| Non-responders | 13 | 0 |
| Responders | 14 | 9 |

Fisher's exact test p-value = 0.01361

Determination of Prognosis Based on Expression of Eight Genes—Two-Class Assignment Model Eighteen selected genes were quantified in all 55 ccRCCs by qPCR and the correlation of expressions between qPCR and DASL platforms was calculated to determine those genes with the best performance on the qPCR platform, thus embodying the ideal nature of a prognostic gene determined on a distinct platform. Univariate logistic correlation analysis for qPCR gene expression with DASL prognosis subtype classification showed that their direction of association was as expected and significant for most prognostic genes (Table 6 and FIG. 4), Eight genes with the highest correlation were selected as the final prognostic gene set. These included CKCL5, EFNA5, EMCN, LAMB3, PLG, PRAME, RARRES1 and SLC6A19.

The linear discriminant analysis (LDA) method was employed to develop a model for assigning prognostic subtype, the categorical dependent variable, based on the linear combination of qPCR expression values of eight genes. The model was trained on qPCR expression data for eight genes in the initial screening cohort of 55 samples for which prognostic class assignment was derived from hierarchical clustering of the DASL dataset. The coefficients of linear discriminants for the eight prognostic genes are in Table 10. The projection of samples onto linear discriminant coordinate is achieved simply by summing up the values of gene expression multiplied by the relevant LDA coefficient as per Table 10. The pre-determined centroids of the two prognostic classes with LDA projection values are 0.781 for good prognosis and 0.228 for poor prognosis. It follows that a sample is assigned to either prognosis group based on the nearness of its LDA projection to either centroid value.

The following description summarizes the method of prognostic class assignment based on expression of eight genes:

ld=["CXCL5"]*0.01822631+["EFNA5"]*0.03641317+ ["EMCN"]*−0.07433829+["LAMB3"]*0.05900340+ ["PLG"]*−0.05058604+["PRAME"]*0.13194489+ ["RARRES1"]*0.05541879+["SLC6A 19"]*−0.10545562

If for a given sample, the distance of calculated ld from centroid1 is less than its distance from centroid2 the sample belongs to good prognosis group i.e. if (abs(ld−centroid1) <abs(ld−centroid2)).

If for a given sample distance of calculated ld from centroid2 is less than its distance from centroid1 the sample belongs to poor prognosis group i.e. if (abs(ld−centroid1) >abs(ld−centroid2)).

TABLE 10

Coefficients of linear discriminants for eight genes in LDA model for ccRCC prognostic subtype assignment

| Gene | Coefficients |
|---|---|
| CXCL5 | −0.0182 |
| EFNA5 | −0.0364 |
| EMCN | 0.0743 |
| LAMB3 | −0.0590 |
| PLG | 0.0506 |
| PRAME | −0.132 |
| RARRES1 | −0.055 |
| SLC6A19 | 0.105 |

The output from an LDA prediction based on the expression of eight genes can be converted to a continuous score, rather than a discrete two-class assignment. This involves normalization of the output ld, described above, to a scale that lies from 1 to 100. The two extremes (minv and maxv) of the LDA projection are first estimated based on the centroid1=0.781 and centroid2=0.226 as follows:

distance=abs(centroid1−centroid2)

min $v$=centroid2−(distance/2.0);

max $v$=centroid1−(distance/2.0);

range=max $v$−min $v$

The two ends of the LDA projection are scaled to lie on a linear scale of 1-100 and a particular sample's calculated ld score is converted to a score between 1 and 100 as follows:

score=(int)(((ld−min $v$)/range)*99.0)+1;

score=min(rk, 100); if score exceeds 100, it is forced to be 100 score=max(rk, 1); if score is less than 1, it is forced to be 1

This is a simple mathematical manipulation of the LDA prediction output that provides a continuous score rather than discrete class assignment.

The performance of the eight-gene prognostic algorithm was validated in a separate cohort of 224 ccRCCs, SGH-224

Figure 6:
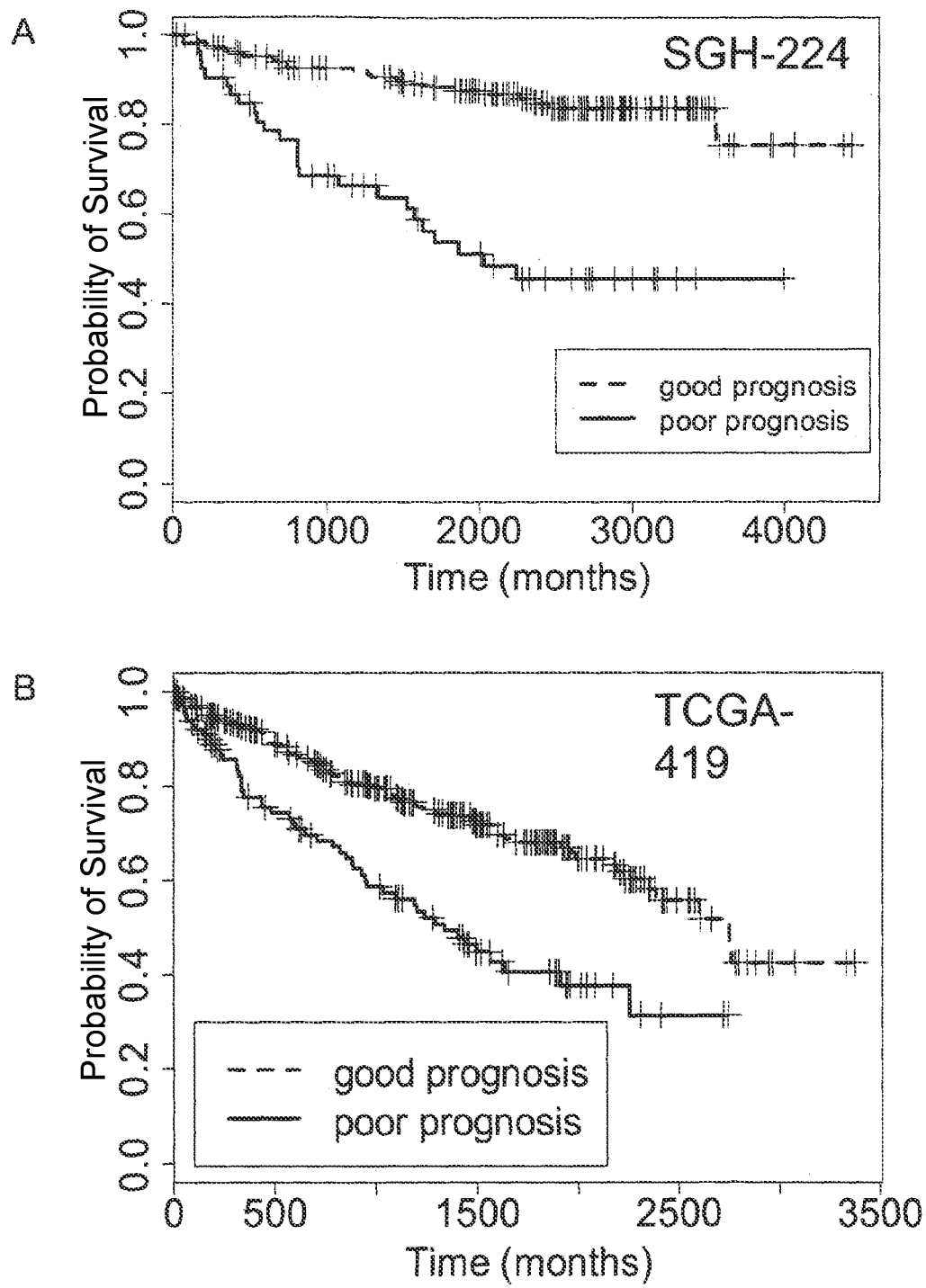
FIG. 6A to 6C. Validation of an eight-gene, prognosis subtype-classification algorithm for clear cell renal cell carcinomas (ccRCC).
Figure 6:
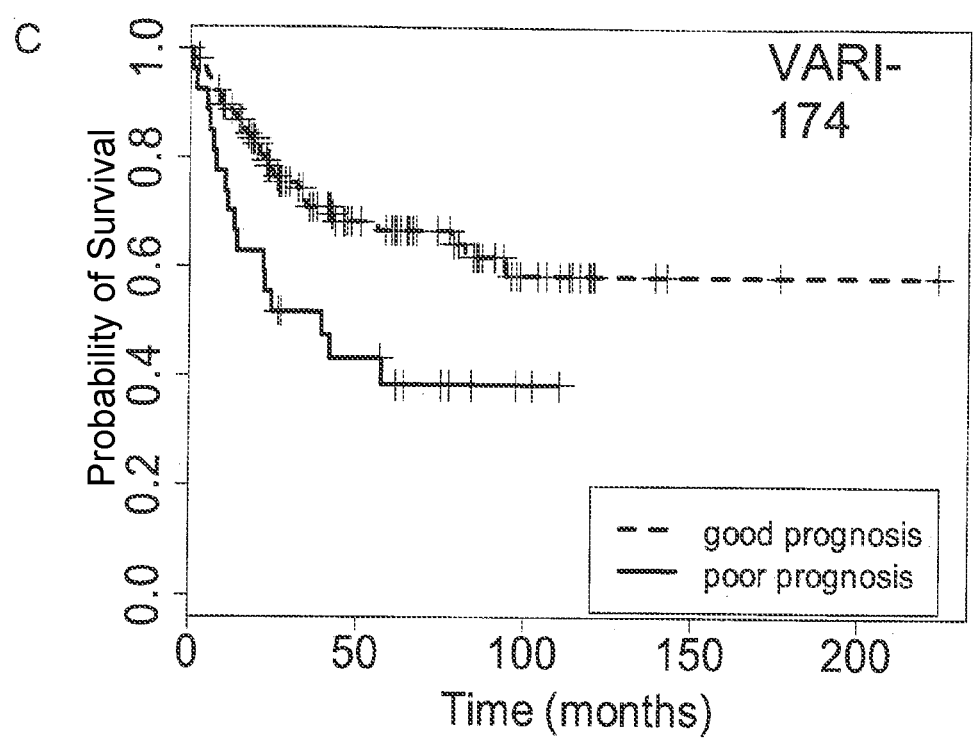

(FIG. 6A). Samples were categorically assigned to good or poor prognosis subtypes based on classification by the prognostic algorithm. Kaplan-Meier analysis showed a significant difference in disease-specific survival between good- and poor-prognosis subtypes (median survival times not reached vs. 67.6 months respectively, HR 4.44 CI 2.53-7.81, p=1.49×10$^{-8}$) (FIG. 6A). Multivariate analysis by Cox proportional hazards modeling demonstrated that the prognostic class assignment as a discrete variable remained significant after adjusting for individual standard clinicopathologic parameters, including age, tumour stage and grade (Table 11).

TABLE 11

Multivariate survival analysis of eight-gene prognostic subtype classifier and clinicopathologic features

| Adjusted variable | Adjusted HR | 95% confidence intervals | p-value LR test |
|---|---|---|---|
| Unadjusted eight-gene prognostic classifier | 4.44 | 2.53-7.81 | 5.72 × 10$^{-7}$ |
| Age | 3.96 | 2.24-6.99 | 1.12 × 10$^{-7}$ |
| Stage | 1.89 | 1.03-3.46 | 0 |
| Grade | 2.86 | 1.51-5.28 | 8.85 × 10$^{-8}$ |

HR = hazard ratio; LR = likelihood ratio.

In order to demonstrate its utility and validate it in a multiple-centre, multiple-platform setting, the eight-gene prognostic algorithm was applied to the TCGA-419 dataset. Kaplan-Meier analysis confirmed that survival was significantly different between the prognostic, subtypes (median survival times 91.7 vs. 44.6 months, HR 2.26 CI 1.59-3.21, p=3.04×10$^{-6}$ by log rank test) (FIG. 6B). Similarly, in a microarray dataset (VARII-174) prognostic subtype classification based on using the log 2-transformed expression values separated samples into two groups with distinctly divergent survival (median survival times not reached vs. 39.6 months, HR 2.19 CI 1.22-3.93, p=0.00743 by log rank test) (FIG. 6C).

For a subset of 48 metastatic RCC patients from SGH-224 cohort receiving tyrosine kinase inhibitor treatment in first-, second- or third-line setting, prognostic classification using eight genes algorithm was done. Characteristics of TKI-receiving patients are available in Table 12. There was a statistically significant difference between number of clinical responders in the two prognostic groups (Table 13) (response rates 67% vs. 100%, p=6.24×10$^{-4}$ by Fisher's exact test). Further, univariate logistic regression analysis with clinical benefit as a categorical variable and prognostic class assignment showed a significant correlation between the two (OR 0.429, p=5.96×10$^{-4}$).

TABLE 12

Characteristics of patients receiving TKI treatment from SGH-224 FFPE validation group

| Number of samples | | 48 |
|---|---|---|
| Age | Range | 43-86 |
| | Median | 57.5 |
| Gender-n (%) | Male | 39 (81.3%) |
| | Female | 9 (18.7%) |
| Stage-n (%) | I | 14 (8.3%) |
| | II | 8 (16.6%) |
| | III | 13 (27.1%) |
| | IV | 23 (47.9%) |

TABLE 12-continued

Characteristics of patients receiving TKI treatment from SGH-224 FFPE validation group

| Tumour T stage-n (%) | 1 | 5 (10.4%) |
|---|---|---|
| | 2 | 15 (31.2%) |
| | 3 | 24 (50%) |
| | 4 | 1 (2.1%) |
| | X | 3 (6.3%) |
| Tumour M stage-n (%) | 0 | 24 (50%) |
| | 1 | 23 (47.9%) |
| | X | 1 (2.1%) |
| Tumour Grade-n (%) | 1 | 1 (2.1%) |
| | 2 | 15 (31.3%) |
| | 3 | 18 (37.5%) |
| | 4 | 13 (27.1%) |
| | Unknown | 1 (2.1%) |
| Primary tumour size | Range | 4-25 |
| | Median | 9 |
| ECOG Performance Status-n (%) | 0 | 20 (41.7%) |
| | 1 | 13 (27.1%) |
| | 1+ | 1 (2.1%) |
| | 2 | 1 (2.1%) |
| | Unknown | 13 (27.1%) |
| Follow-up duration (yr) | Range | 0.19-12.3 |
| | Mean | 3.71 |
| Patient Status-n (%) | Deaths (cancer-related) | 28 (58.3%) |
| | Death (other causes) | 1 (2.1%) |
| | Alive with disease | 18 (37.5%) |
| | No evidence of disease | 1 (2.1%) |
| Post-nephrectomy treatment-n (%) | Sunitinib First line | 32 (66.7%) |
| | Second line | 5 (10.4%) |
| | Third line | 5 (10.4%) |
| | Pazopanib First line | 5 (10.4%) |
| | Second line | 1 (2.1%) |
| Previous nephrectomy MSKCC risk factors | good | 36 (75%) |
| | intermediate | 11 (22.9%) |
| | poor | 21 (43.8%) |
| | unknown | 13 (27.1%) |
| | | 3 (6.3%) |

TABLE 13

Clinical response count data for 48 TKI-receiving patients classified based on eight-gene prognostic algorithm

| | Good prognosis subtype | Poor prognosis subtype |
|---|---|---|
| Patients with clinical benefit | 19 | 16 |
| Patients with progressive disease[†] | 0 | 12 |

Fisher's exact test p-value = 6.237 × 10$^{-4}$
[†]Patients with progressive disease were those for whom disease progressed as evaluated radiologically, after initiating TKI treatment. Patients with clinical benefit were those that showed partial response to TKI therapy or had stable disease-after initiating TKI therapy, as evaluated radiologically. One patient had non-evaluable response data.

A practical molecular assay has been developed that is capable of stratifying ccRCC patients into prognostic groups that are essentially manifestations of the underlying biological heterogeneity of ccRCC. The prognostic assay also functions well as a predictive assay for clinical response to TKI therapy, suggesting a fundamental overlap between patients with good prognosis and those likely to respond to therapy upon relapse. This assay therefore can delineate an aggressive subtype of the disease, which patients prognosed with, face worse survival outcomes and are also unlikely to benefit from TKI therapy.

Previous efforts to develop a multigene assay for prognostic classification of ccRCC have identified 16 genes, expression levels of which were associated with recurrence-free interval. Of note, in this previous study, prognostic genes were selected from a predetermined set of 732 genes, based on their function and individual association with recurrence-free interval. In contrast, in this study the choice of prognostic genes was driven by the identification of gene expression-based subtypes of ccRCC, without the introduction of previous knowledge of gene function or clinical outcome. With this truly unbiased approach to gene selection unraveling the latent differences among ccRCC, the selected prognostic genes are more likely to continue to embody these differences even in smaller numbers as in a multigene assay.

The choice of FFPE material to develop and confirm the prognostic assay allows greater scope for validation on a large-scale given the relative abundance of such material. Several studies in the past have molecularly profiled ccRCCs to identify subtypes with differing outcomes. However, all have made use of fresh-frozen material limiting the validation of identified prognostic gene signatures.

The platform used for initial screening of potential prognostic genes was the whole-genome high-throughput Illumina's DASL analysis but the final platform qPCR was chosen to confirm and validate the prognostic assay. Although the success rate of translation to the qPCR platform from the DASL platform was relatively low (10 out of 37 genes tested=27%), the ability of the final selected gene set to discriminate prognostic groups in the validation group using the qPCR platform reinforces the platform-independence of the assay. The qPCR platform is preferable for a prognostic assay as it is practical, inexpensive, flexible and readily transferable to other laboratories.

The 10 genes finally selected to be included in the prognostic assay, CXCL5, EFNA5, EMCN, IGFBP1, LAMB3, MMP9, PLG, PRAME, RARRES1 and SLC6A19, represent genes from the chemokine signaling, migration and invasion, angiogenesis, growth factor signaling, ECM-interacting, retinoic acid signaling and transporter families. Given the non-predeterministic manner in which they were selected the wide variety of cellular functions encompassed by the prognostic genes is not surprising. Notwithstanding, the biological subtypes of ccRCC likely differ in the pathway functions described here.

The prognostic algorithm developed based on 10 genes was initially applied to the 55 ccRCCs in the screening cohort that also served as the confirmation cohort. The purpose was to identify a suitable cutoff for the score such that the best discrimination of prognostic groups was achieved. The cutoff chosen represents the score at which reasonably high level of concordance of sample assignment to class was achieved by both DASL and qPCR platforms. This cutoff score may be subject to refinement as more samples from independent study centres are analyzed with this assay for prognostic classification.

An additional utility of the 10-gene prognostic assay was the ability to predict benefit from TKI therapy, measured as objective response assessed by tumour shrinkage. A prognostic assay can serve as a predictive assay, if the prognostic subtypes represent biological subtypes of the disease with differential disease progression and accompanying susceptibility to therapeutic intervention. Previous attempts to identify predictive biomarkers for TKI therapy for ccRCC, which is the most common therapy administered presently have looked at baseline levels of cytokine and angiogenic factors in plasma and serum, levels of factors involved in VEGF signaling pathways in plasma, immunohistochemical analyses of HIF-1α, CAIX, PTEN and p21 in primary tumours. Association of genetic polymorphisms with response to sunitinib has been extensively analyzed for targets of sunitinib (VEGFRs, PDGFRs) and drug metabolism genes and with pazopanib for angiogenesis- and exposure-related genes. Most of these studies looked at the progression-free survival times after drug administration, but did not address the objective response criteria, which is more relevant in the clinical setting for decision-making. Progression-free survival time can indicate association of drug-response with specific factors but may ultimately arise from different underlying ccRCC biology, which is what was sought to be identified in this study.

This simple 10-gene based assay that can run on FFPE material of primary and metastatic tumours can thus define subsets of biologically distinct ccRCCs. Using a prognostic risk scoring system, patients can be stratified to an aggressive subtype which are likely to face poor clinical outcome in the localized setting and also less likely to benefit from TKI therapy in the metastatic setting.

The invention claimed is:

1. A method of treating a patient having renal cancer comprising the steps of:
   a) obtaining a tumor tissue sample from the patient,
   b) detecting the level of expression for each marker of a panel of markers, wherein the panel comprises at least one housekeeping gene selected from the group consisting of ACTB, RPL13A, RPL9, and RPS29, or any combinations thereof; and prognostic genes CXCL5, EFNA5, EMCN, LAMB3, PLG, PRAME, RARRES1, and SLC6A19;
   c) comparing the level of expression of each marker with a predetermined reference level associated with each marker to obtain an expression parameter, wherein the predetermined reference level is based on the expression of the at least one housekeeping gene, and wherein said comparison comprises normalizing the expression level of each marker with the predetermined reference level; and
   d) determining the differential expression of each marker in the tumor tissue sample based on the expression parameter for each marker,
   e) administering an effective amount of Tyrosine Kinase Inhibitor (TKI) therapy if the patient exhibits at least a doubling of expression level for EMCN, PLG and SLC6A19 markers, or at least a halving of expression level for CXCL5, EFNA5, LAMB3, PRAME and RARRES1 markers,
   or
   administering a different anti-renal cancer treatment if the patient does not exhibit at least a doubling of expression level for EMCN, PLG and SLC6A19 markers, or does not exhibit at least a halving of expression level for CXCL5, EFNA5, LAMB3, PRAME and RARRES1 markers,
   wherein the renal cancer is clear cell renal cell carcinoma (ccRCC) or a mixture of renal tumors comprising ccRCC, and the patient suffers from ccRCC, or the patient suffers from ccRCC and undergoes anti-cancer treatment.

2. The method according to claim 1, wherein the tumor tissue sample is obtained from tissue selected from the group consisting of frozen tissue, tissue biopsies, circulating tumor cells, and bodily fluids selected from the group consisting of ascites, effusions, cerebrospinal and urine.

3. The method according to claim 1, wherein the patient having renal cancer is a patient that has previously received and/or is currently undergoing-anti-cancer treatment;
   wherein the anti-cancer treatment is selected from the group consisting of a chemotherapeutic treatment, a surgical treatment, a treatment with radiation therapy, immunotherapy, targeted therapy, a small molecule therapeutic or any combination thereof;
   wherein if the anti-cancer treatment comprises a chemotherapeutic treatment, then the chemotherapeutic treatment comprises treatment with a protein kinase inhibitor, receptor tyrosine kinase inhibitor, antimetabolite, platinum complex, spindle poison, DNA crosslinking drug and alkylating agent, bleomycin, antibiotic, and topoisomerase inhibitor or combinations thereof;
   wherein if the chemotherapeutic treatment comprises treatment with a receptor tyrosine kinase inhibitor, then the receptor tyrosine kinase inhibitor is selected from the group consisting of sunitinib, pazopanib, axitinib, sorafenib or combinations thereof;
   wherein if the chemotherapeutic treatment comprises treatment with a protein kinase inhibitor, then the protein kinase inhibitor is temsirolimus or everolimus;
   wherein if the anti-cancer treatment comprises a targeted therapy, then the targeted therapy comprises anti-tumor antibodies such as bevacizumab, interferon and combinations thereof;
   wherein if the anti-cancer treatment comprises immunotherapy, then the immunotherapy is interferon, high-dose-interleukin 2 or combinations thereof; and
   wherein if the anti-cancer treatment comprises a small molecule therapeutic, then the small molecule therapeutic comprises tivozantinib.

4. The method of claim 1, wherein the at least one housekeeping gene comprises ACTB, RPL13A, RPL9, and RPS29 and the predetermined reference level is the average expression level of the four housekeeping genes.

5. The method of claim 1, the predetermined reference level is the geometric mean $C_T$ value of the at least one housekeeping gene.

6. The method according to claim 1, wherein detecting the level of expression for each marker comprises:
   a. contacting a nucleic acid sequence obtained or derived from said sample with at least one primer and/or at least one probe for amplification of a sequence of the marker;
   b. amplifying said nucleic acid sequence using said at least one primer or probe with a polymerase enzyme; and
   c. detecting the level of expression of the marker in said sample.

7. The method of claim 1, wherein the TKI therapy is selected from the group consisting of sunitinib, pazopanib, axitinib, sorafenib, or combinations thereof.

* * * * *